US012758600B2

(12) United States Patent
Hope

(10) Patent No.: US 12,758,600 B2
(45) Date of Patent: Oct. 13, 2026

(54) SYSTEMS, METHODS, AND COMPOSITIONS FOR TREATING OR PREVENTING BACTERIAL INFECTION AND FOR REDUCING OR PREVENTING BACTERIAL OVERPOPULATION

(71) Applicant: BRIGHAM YOUNG UNIVERSITY, Provo, UT (US)

(72) Inventor: Sandra Hope, Provo, UT (US)

(73) Assignee: BRIGHAM YOUNG UNIVERSITY, Provo, UT (US)

( * ) Notice: Subject to any disclaimer, the term of this patent is extended or adjusted under 35 U.S.C. 154(b) by 1066 days.

(21) Appl. No.: 17/259,711

(22) PCT Filed: Jul. 12, 2019

(86) PCT No.: PCT/US2019/041687
§ 371 (c)(1),
(2) Date: Jan. 12, 2021

(87) PCT Pub. No.: WO2020/014662
PCT Pub. Date: Jan. 16, 2020

(65) Prior Publication Data

US 2021/0138006 A1 May 13, 2021

Related U.S. Application Data

(60) Provisional application No. 62/697,819, filed on Jul. 13, 2018.

(51) Int. Cl.
*A61P 31/04* (2006.01)
*A61K 35/74* (2015.01)
*A61K 35/76* (2015.01)

(52) U.S. Cl.
CPC .............. *A61K 35/76* (2013.01); *A61K 35/74* (2013.01); *A61P 31/04* (2018.01)

(58) Field of Classification Search
CPC ........ A61K 35/76; A61K 35/74; A61K 39/07; A61P 31/04
See application file for complete search history.

(56) References Cited

U.S. PATENT DOCUMENTS 5,792,625 A * 8/1998 Klaenhammer ......... C12N 9/22 435/71.1
2015/0050717 A1 2/2015 Collins et al.
2016/0309723 A1* 10/2016 Gonzalez ............... A01N 63/40
2018/0140698 A1 5/2018 Cube et al.

FOREIGN PATENT DOCUMENTS

WO WO-2007133730 A2 * 11/2007 ............. C12N 15/86

OTHER PUBLICATIONS

Duckworth et al., Biodrugs, 16 (1):57-62 (2002) (Year: 2002).*
Oliver et al., Science, 325:992-994 (2009) (Year: 2009).*
Payne et al., Clin. Pharmacol. Ther., 68:225-230 (2000) (Year: 2000).*
Payne et al., J. Theor. Biol., 208:37-48 (2001) (Year: 2001).*
Tsonos et al., Vet. Microbiol., 171:460-469 (2014) (Year: 2014).*
Ruiu, Insects, 4:476-492 (2013) (Year: 2013).*
Berg et al., PLoS ONE 11(6):1-24 (2016) (Year: 2016).*
Djukic et al., PLoS ONE 9(3):1-14 (2014) (Year: 2014).*
Lehman, Development of a Bacteriophage-based pesticide for fire blight, Thesis , p. 1-310 (Year: 2007).*
International Search Report and Written Opinion dated Sep. 24, 2019, issued in PCT Application No. PCT/US2019/041687, filed Jul. 12, 2019.
Thomas S. Brady, *Bacteriophages for Treating American Foulbrood and the Neutralization of Paenibacillus Larvae Spores*, Jul. 1, 2018, retrieved Sep. 16, 2019 https://www.google.com/search?rlz= 1 C 1 SQJL_ enUS861 US861&tbs=qdr%3Ay15&ei=BMR_ XeG2Gcm4tQXT1 rroAQ&q=Bacteriophages+for+ Treating+American+Foulbrood+and+the+Neutralization+of+Paenibacillus+larvae+Spores&oq=Bacteriophages+for+ Treating+American+Foulbrood+and+the+Neutralization+of+Paenibacillus+larvae+Spores&gs_I=psy-ab.3 . . . 2974.2974 . . 4594 . . . 0.0 .. 0.85.85.1 . . . 0 . . 1 .. gws-wiz.fn6JQRF3iYs&ved= 0ahUKEwjhyPHI7NXkAhVJXK0KHVOrDh0Q4d UDCAs&uact=5; entire document, especially abstract; p. 21 para 2, p. 23 para 1, p. 29 para 1-3, p. 72 para 1.

* cited by examiner

*Primary Examiner* — Melenie L Gordon
*Assistant Examiner* — Tiffany M Gough
(74) *Attorney, Agent, or Firm* — Workman Nydegger

(57) ABSTRACT

Kits for use in treating or preventing an infection caused by a primary bacterium or for use in reducing or preventing overpopulation of the primary bacterium can include a bystander bacterium having a genomically-encoded bacteriotoxin specific for at least the primary bacterium and a first bacteriophage tropic for the bystander bacterium. The bystander bacterium can be provided as a live culture and infection of the bystander bacterium by the first bacteriophage causes expression of the genomically-encoded bacteriotoxin. Methods of treating or preventing an infection caused by a primary bacterium or for reducing or preventing overpopulation of the primary bacterium can include administering a bacteriophage tropic for a bystander bacterium that has a genomically-encoded bacteriotoxin that is expressed upon infection by the first bacteriophage and is specific for at least the primary bacterium.

6 Claims, 5 Drawing Sheets

SYSTEMS, METHODS, AND COMPOSITIONS FOR TREATING OR PREVENTING BACTERIAL INFECTION AND FOR REDUCING OR PREVENTING BACTERIAL OVERPOPULATION

BACKGROUND

Diseases caused by pathogenic bacteria are known to be a serious problem to various species in the plant and animal kingdoms. For example, American Foulbrood (AFB) is a devastating disease in honeybees that is caused by the endospore-forming bacterial pathogen *Paenibacillus larvae*, and in the United States alone, AFB results in the loss of millions of dollars annually. *P. larvae* endospores are inadvertently spread from the environment or other infected hives to honeybee larvae by the worker bees that are feeding them. Honeybee larvae die as endospores germinate and bacteria grow within the larval cells. These pathogenic bacteria liquefy the larvae producing a viscous, spore-laden fluid, and the disease rapidly spreads in the hive and most often leads to a quick death of the colony.

Terramycin and Tylosin are commonly used as preventative antibiotic treatments for AFB in the spring and fall seasons, as well as being the preferred antibiotic for treatment upon infection. Problematically, however, most strains of *P. larvae* in the United States are resistant to Terramycin and Tylosin-resistant *P. larvae* strains have recently been observed. Because these antibiotics are in the tetracycline family and can negatively impact pregnant women and children, their use is generally limited to the non-honey-producing seasons, or when used during honey-production, the honey is discarded as a precautionary measure. Honeybee hives affected by AFB typically do not survive without treatment, and hives that do not recover after antibiotic treatment must be destroyed by fire to prevent the spread or further infestation. Yet even when used to treat or prevent AFB, these broad-spectrum antibiotics negatively affect the homeostasis of the honeybees' natural gut microbiota, making them more susceptible to infection by *Nosema* sp. microsporidia.

American Foulbrood may be transferred and initiated only by *P. larvae* endospores. Owing to the hardy nature of endospores, *P. larvae* endospores can remain viable and last indefinitely on beekeeping equipment. This poses an additional concern as the disease is extremely contagious and easily spread via contaminated equipment, hive tools, or even the beekeeper's hands. In the past, the best way to manage American Foulbrood was simply to avoid it altogether.

The arsenal of effective antibiotics for treating AFB—and other bacterial infections in animals and plants—is dwindling, and more effective systems and methods of treating diseases caused by pathogenic/opportunistic bacteria are needed. Further, methods and systems are needed that are efficient at treating or preventing bacterial infections or for reducing or preventing overpopulation of pathogenic or opportunistic pathogenic bacteria.

BRIEF SUMMARY

Embodiments of the present disclosure solve one or more of the foregoing or other problems in the art with systems and methods for affecting the number and/or concentration of bacteria, preferably pathogenic bacteria, in a targeted manner and can be used to treat or prevent bacterial infections in non-human animals and plants. In particular, one or more implementations can include a kit for use in treating or preventing an infection caused by a primary bacterium or for use in reducing or preventing overpopulation of the primary bacterium. In one aspect, the kit includes a bystander bacterium having a genomically-encoded bacteriotoxin specific for at least the primary bacterium. The bystander bacterium can be provided as a live culture in the kit. The kit can additionally include a first bacteriophage tropic for the bystander bacterium, wherein infection of the bystander bacterium by the first bacteriophage causes expression of the genomically-encoded bacteriotoxin.

In one aspect, the kit includes a second bacteriophage tropic for the primary bacterium.

In one aspect, the kit includes a cocktail of bacteriophages comprising the first bacteriophage with each bacteriophage in the cocktail being tropic for the bystander bacterium. Additionally, each bacteriophage in the cocktail of bacteriophages can genomically encode a bacteriotoxin specific for at least the primary bacterium.

In one aspect, the kit includes at least one of a probiotic or prebiotic.

In one aspect, the kit includes a second bystander bacterium that also has a genomically-encoded bacteriotoxin specific for at least the primary bacterium. The kit can additionally include a bacteriophage tropic for the second bystander bacterium, wherein infection of the second bystander bacterium by the bacteriophage causes expression of the genomically-encoded bacteriotoxin. In one aspect, the bacteriophage tropic for the second bystander bacterium is the first bacteriophage. In another aspect, the bacteriophage tropic for the second bystander bacterium is different than the first bacteriophage.

In one aspect, the bystander bacterium is disposed in a first liquid composition and the first bacteriophage is disposed in a second, separate liquid composition.

In one aspect, at least one of the bystander bacterium and the first bacteriophage is disposed in a solid composition.

In one aspect, the bystander bacterium is disposed in a first solid composition and the first bacteriophage is disposed in a second solid composition and the first and second solid compositions are co-formulated.

Embodiments of the present disclosure additionally include compositions for use in treating or preventing an infection caused by a primary bacterium or for use in reducing or preventing overpopulation of the primary bacterium. In one aspect, the composition includes a first bacteriophage tropic for a bystander bacterium that has a genomically-encoded bacteriotoxin specific for at least the primary bacterium that is expressed upon infection by the first bacteriophage.

In one aspect, the composition includes a second bacteriophage tropic for the bystander bacterium.

In one aspect, the composition includes a second bacteriophage tropic for a second bystander bacterium that also has a genomically-encoded bacteriotoxin specific for at least the primary bacterium.

In one aspect, the composition includes the bystander bacterium co-formulated with the first bacteriophage. The composition can, in one aspect, be in solid form. In another aspect, the composition is in liquid form.

Embodiments of the present disclosure additionally include methods of treating or preventing an infection caused by a primary bacterium or for use in reducing or preventing overpopulation of the primary bacterium. An exemplary method includes the act of administering a bacteriophage tropic for a bystander bacterium where the bystander bacterium has a genomically-encoded bacteriotoxin that is expressed upon infection by the bacteriophage and is specific for at least the primary bacterium.

In one aspect of the exemplary method, administering the bacteriophage includes administering the bacteriophage to a plant associated with the primary bacterium. In another aspect of the exemplary method, administering the bacteriophage includes administering the bacteriophage to a non-human animal associated with the primary bacterium, preferably a non-mammalian animal associated with the primary bacterium. In either of the foregoing aspects, the methods can additionally include administering the bystander bacterium. Alternatively, administering the bacteriophage can include administering a cocktail of bacteriophages that includes the bacteriophage. Additionally, aspects of the disclosed methods can include administering one or more bystander bacterium that each genomically encodes a bacteriotoxin that is expressed upon infection by a tropic bacteriophage of the cocktail of bacteriophages and that is specific for at least the primary bacterium. In such an exemplary aspect, the administered cocktail of bacteriophages are tropic for the one or more administered bystander bacterium.

This summary is provided to introduce a selection of concepts in a simplified form that are further described below in the detailed description. This summary is not intended to identify key features or essential features of the claimed subject matter, nor is it intended to be used as an indication of the scope of the claimed subject matter.

Additional features and advantages of the disclosure will be set forth in the description which follows, and in part will be obvious from the description, or may be learned by the practice of the disclosure. The features and advantages of the disclosure may be realized and obtained by means of the instruments and combinations particularly pointed out in the appended claims. These and other features of the present disclosure will become more fully apparent from the following description and appended claims or may be learned by the practice of the disclosure as set forth hereinafter.

BRIEF DESCRIPTION OF THE DRAWINGS

In order to describe the manner in which the above recited and other advantages and features of the disclosure can be obtained, a more particular description of the disclosure briefly described above will be rendered by reference to specific embodiments thereof, which are illustrated in the appended drawings. It is appreciated that these drawings depict only typical embodiments of the disclosure and are not therefore to be considered to be limiting of its scope. The disclosure will be described and explained with additional specificity and detail through the use of the accompanying drawings in which.

DETAILED DESCRIPTION

Figure 1:
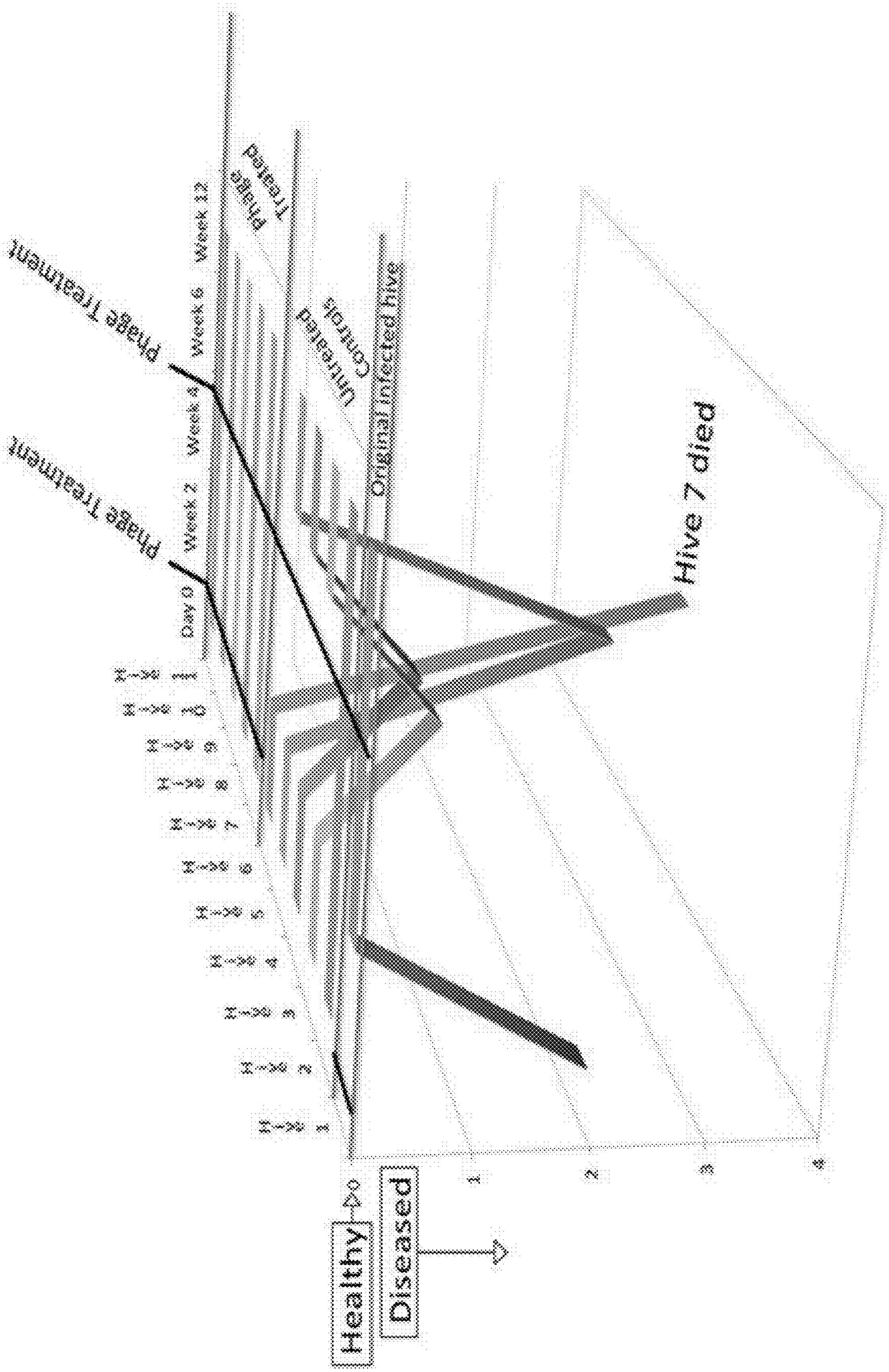
FIG. 1 is a graph illustrating the results of *Paenibacillus larvae* phage treatment on infected and at-risk beehives in accordance with the teachings and principles of the disclosure.

Before describing various embodiments of the present disclosure in detail, it is to be understood that this disclosure is not limited to the parameters of the particularly exemplified systems, methods, apparatus, products, processes, and/or kits, which may, of course, vary. Thus, while certain embodiments of the present disclosure will be described in detail, with reference to specific configurations, parameters, components, elements, etc., the descriptions are illustrative and are not to be construed as limiting the scope of the claimed invention. In addition, the terminology used herein is for the purpose of describing the embodiments and is not necessarily intended to limit the scope of the claimed invention.

Furthermore, it is understood that for any given component or embodiment described herein, any of the possible candidates or alternatives listed for that component may generally be used individually or in combination with one another, unless implicitly or explicitly understood or stated otherwise. Additionally, it will be understood that any list of such candidates or alternatives is merely illustrative, not limiting, unless implicitly or explicitly understood or stated otherwise.

In addition, unless otherwise indicated, numbers expressing quantities, constituents, distances, or other measurements used in the specification and claims are to be understood as being modified by the term "about," as that term is defined herein. Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Any headings and subheadings used herein are for organizational purposes only and are not meant to be used to limit the scope of the description or the claims.

Exemplary Embodiments

As discussed above, clinically approved antibiotics have been a mainstay for combatting bacterial infections for decades. On the whole, they have been prescribed with restraint and responsibility on the part of physicians treating human patients that suffer from bacterial infections. However, whether the result of patients often failing to self-administer the entire antibiotic regimen as instructed or whether as a result of their widespread adoption and use in clinical practice, antibiotic resistance of bacterial pathogens remains on the rise. Fewer and fewer commercial antibiotics are available as bacterial pathogens become ever more resistant to the remaining arsenal of clinically approved antibiotics.

Commercial antibiotics have been more widely used—often with less restraint—in plants and animals. In particular, antibiotics are commonly used without professional advice or instruction to treat bacterial infections in plants and animals, and while less common in human treatment regimens, it is commonplace to prophylactically treat plants and animals with antibiotics in an attempt to ward off possible infection. Unsurprisingly, commercial antibiotics are becoming less effective in the agricultural and animal husbandry industries as the historically sensitive pathogens are gaining resistance.

Notwithstanding the foregoing, even the remaining set of effective commercial antibiotics are problematic as most, if not all, are considered broad-spectrum antibiotics and therefore non-specifically target beneficial probiotic and commensal bacteria—not just pathogens. The importance and effects of a diverse and consistently populated microbiome on the health of its host organism are just recently being appreciated. The microbiome can influence nutrient uptake and host physiologic processes, including metabolism and immunity. Additionally, a diverse and consistently populated microbiome of natural commensal bacteria, fungi, and viruses, acts as a physical barrier that precludes the colonization and/or spread of pathogens, including, for example, opportunistic pathogens. Indeed, as in the exemplary instance discussed above, use of broad-spectrum antibiotics on honeybees (e.g., to treat or prevent *P. larvae* infections) disrupts the homeostatic microbiome of the honeybee and thereby makes them more susceptible to infection by *Nosema* sp. microsporidia.

Accordingly, there is an outstanding need for systems and methods for treating or preventing bacterial infections in plants and non-human animals and/or for reducing or preventing the overpopulation of bacterial pathogens, particularly opportunistic pathogens.

Figure 6:
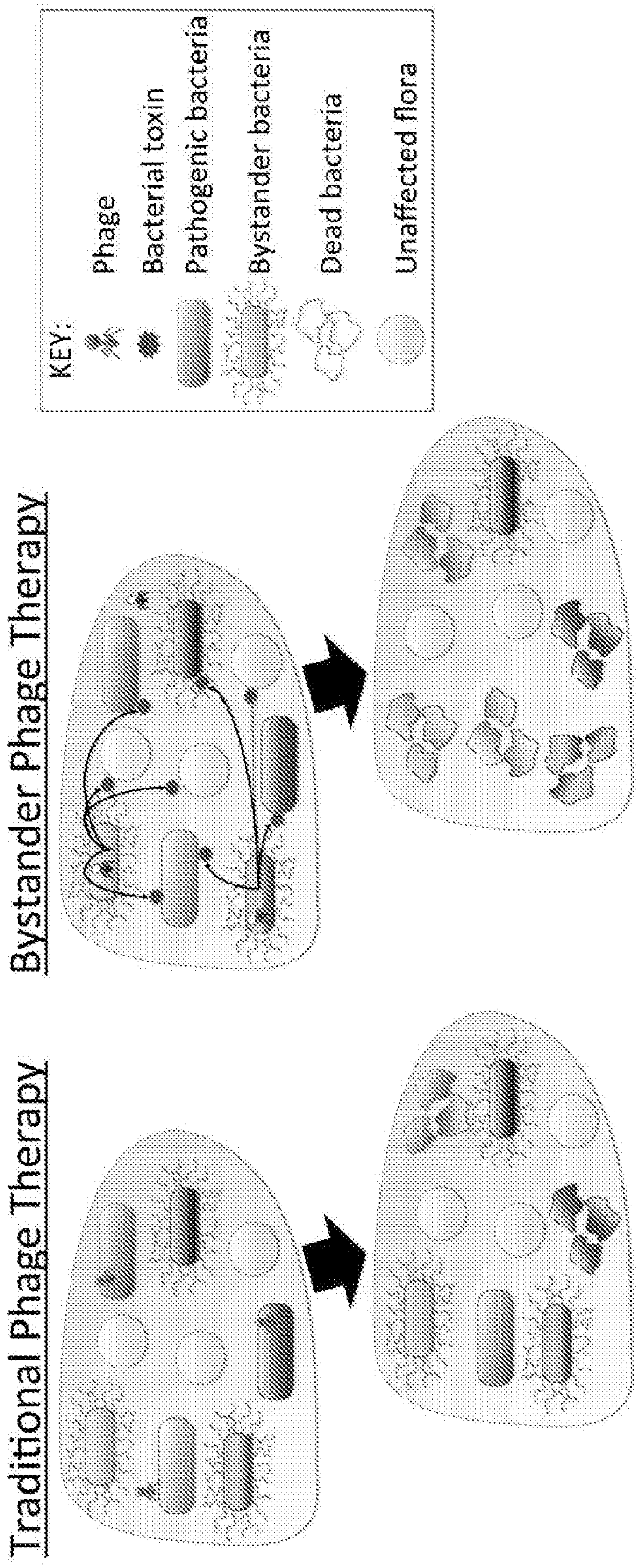
FIG. 6 illustrates a comparative model of traditional and bystander phage therapies in accordance with teachings and principles of the disclosure.

The systems and methods disclosed herein address some of the foregoing deficiencies in the art and beneficially enable more targeted and natural approaches that are less likely to demonstrate pathogen resistance and that are more widely adaptable to various, even disparate systems. In general, the disclosure extends to systems and methods of treating a disease or bacterial infection caused by a primary bacterium by attacking a secondary (or "bystander") bacterium not directly causative of or contributing to the disease or state of infection with an antibacterial agent. The antibacterial agent can include, for example, bacteriophages tropic for at least the secondary bacterium (but preferably not tropic for the bacterial pathogen), and when infected by the bacteriophage, the secondary bacterium responds by upregulating the expression and production of a bacteriotoxin that targets the pathogenic bacterium. In this way, the pathogen becomes collateral damage of the bacteriotoxin produced by the infected secondary bacterium, which leads to or acts to help clear the actual disease. A cartoon comparing the foregoing bystander phage therapy model to the traditional phage therapy model is illustrated in FIG. 6.

Bacteriophages, or "phages," are viruses that infect bacteria. Phages use tail fibers to attach to a bacterial host cell, and it is these tail fibers that affect the specificity, or tropism, of the phage for a given set of bacterial hosts. After attaching, the phage injects its genomic nucleic acid into a host bacterium. At this point, the phage replicates using either a lytic cycle, which typically results in bacterial cell lysis, or a lysogenic (non-lytic) cycle, which leaves the bacterial cell intact. In either case, the phage co-opts the use of bacterial cell machinery to generate multiple phage progeny that can infect the next nearby bacterial target.

Differences in bacteriophage host recognition mainly reflect differences in bacterial cell surface receptors, and as such, the tropism of phages is limited to bacteria and does not extend to plants or animals. Some bacteriophages are understood to have broad microbial tropism, being capable of successfully infecting bacteria from different phylogenetic orders and/or greater than 10, preferably greater than 8, or more preferably greater than 6 different genera and/or species of bacteria within the same phylogenetic order, while other bacteriophages have a narrower tropism, being capable of successfully infecting, preferably, bacteria from the same phylogenetic order, more preferably only select genera and/or species of bacteria. In some instances, a bacteriophage may have a narrow tropism for bacteria derived from a single genera or bacterial species or strain. A bacteriophage having a "narrow tropism" is understood to be capable of successfully infecting less than or equal to 6, preferably less than or equal to 5, or more preferably less than or equal to 4, still more preferably less than or equal to 3, still more preferably less than or equal to 2, most preferably a single bacterial genera and/or species or strain. In some instances, the tropism of a bacteriophage is limited to a single species, genera, or taxonomic family of bacteria.

Bacteriophages having a narrow tropism can be useful to target a single, or narrow range of, bacterial genera and/or species or strain and thereby limit off-target effects and reduce the likelihood of widespread resistance. Further, by targeting a bystander bacterium with a bacteriophage having tropism for the bystander, there is a significantly reduced likelihood that the pathogen will develop a resistance to the phage infection. Further still, the native (or transgenic) bacteriotoxin produced by the bystander bacterium as a result of the phage infection is generated and distributed in situ without the need to purify and administer the bacteriotoxin. This beneficially increases the number and types of effective antibiotics that can be made available for treatment methods and greatly expands the applicability of targeted therapies to bacterial infections in a wide range of plants and non-human animals.

For example, kits for use in treating or preventing an infection caused by a primary bacterium or for use in reducing or preventing overpopulation of the primary bacterium can include a bystander bacterium (e.g., as a live culture) having a genomically-encoded bacteriotoxin specific for at least the primary bacterium. The kit can additionally include a first bacteriophage tropic for the bystander bacterium, wherein infection of the bystander bacterium by the first bacteriophage causes expression of the genomically-encoded bacteriotoxin that targets at least the primary bacterium. Accordingly, when implemented, the first bacteriophage infects the bystander bacterium, causing the bystander bacterium to express bacteriotoxin. The bacteriotoxin is released from the bystander bacterium and subsequently targets the primary bacterium where its toxic effects prevent the primary bacterium from growing and/or cause the death of the primary bacterium.

In essence, kits and compositions of the present disclosure enable the selective targeting of primary (e.g., pathogenic) bacteria through a bystander intermediate. This beneficially enables, among other things, the selection of bystander-phage pairs that are compatible and that can be quickly and inexpensively produced at commercial scale. Further, the bystander bacterium can be genetically modified, or specifically selected for characteristics that are naturally modified, to express any number or type of bacteriotoxins to thereby change the primary bacterium indirectly affected by bacteriophage infection of the bystander bacterium. This allows for the kits, compositions, and methods disclosed herein to be easily tailored to the prevention and/or treatment of a bacterial infection within a wide range of plants and non-human animals.

An additional exemplary benefit of the disclosed kits and compositions is that a bystander bacterium may exist within the microbiome and/or environment of the host affected by the bacterial pathogen (i.e., the primary bacterium). By applying the bacteriophage to the infected area, for example as an oral unit dosage form, as a sprayable composition, or salve, the bacteriophage can infect the resident bystander bacterium to force expression of the bystander's genomically-encoded, pathogen-targeting bacteriotoxin which then kills or prevents the growth of the primary bacterium causative of the infection/disease.

Implementations such as the foregoing may be amplified or honed, for example, by modulating the breadth of bacteriophage tropism to target greater or fewer bystander bacteria. For example, increasing the breadth of tropic phages can lead to targeting a plurality of bystander bacteria (e.g., of different strains, species, genera, or families) and therefore increase the amount or concentration of bacteriotoxin released by the infected bacteria. It may additionally, or alternatively, release a plurality of different bacteriotoxins, which may increase the likelihood the treatment is lethal to the primary bacterium.

The disclosed system and method of treating a disease or bacterial infection can include a single bacteriophage or a cocktail of bacteriophages having overlapping tropism for the target bacterium. When used, a cocktail of phages can maximize the target range and thereby increase the effectiveness of a treatment. In a preferred embodiment, the bacteriophages within a cocktail are additionally selected for those with greater genetic diversity from each other and/or for the mode of attachment or infection. Targeting the same bacterium with a plurality of genetically diverse phages and/or phages having different modes of attachment or infection can beneficially reduce the likelihood of escape mutants within the bacterial populations.

The compositions disclosed herein can be included within a kit that additionally includes a probiotic and/or prebiotic. Alone, a probiotic may not be as effective or have as much of a beneficial effect when the bacteria within the probiotic have to compete with bacteria in the native microbiome of the host. However, when coupled with and/or co-administered with the compositions disclosed herein, the disclosed probiotics can beneficially improve and/or stabilize the host microbiome and provide a healthier and often more diverse microbiome. This may be due, at least in part, to the bacteriophages within the composition clearing niches within the host microbiome previously held by the primary and/or secondary (or "bystander") bacteria. The probiotic microbes can then colonize the newly clearly niches and thereby provide a twofold benefit: preventing the recolonization of pathogens and/or other less beneficial bacteria by occupying the newly cleared niches and providing the host with beneficial nutrients and/or metabolites.

Kits, Systems, and Methods for Treating or Preventing Bacterial Infection of Honeybees In one aspect, kits of the present disclosure include kits for use in the treatment or prevention of American Foulbrood (or other bacterial infection of honeybees) or for use in reducing or preventing overpopulation of *P. larvae* (or other honeybee bacterial pathogen). The kit can include one or more bacteriophage tropic for a bystander bacterium having a genomically-encoded bacteriotoxin specific for at least *P. larvae*. In one embodiment, the one or more bystander bacterium includes *Brevibacillus laterosporus*, particularly strains of *B. laterosporus* having a genomically-encoded bacteriotoxin that is expressed upon infection of *B. laterosporus* by the phage and which targets at least *P. larvae*.

As proof of the foregoing concept, phages were isolated from soil or bee debris samples collected near infected hives. Cultures of the bystander bacterium were used to enrich for any phages in the samples from soil or bee debris. Once captured, each unique phage was purified and amplified to achieve a pure isolation of the single phage type at a concentration of greater than $10^6$ phages per milliliter. The phages were suspended in a typical bacterial growth medium called Porcine Brain-Heart Infusion (PBRI). PBHI contains chemicals considered to be Generally Recognized As Safe (GRAS) including sodium chloride (NaCl), and sodium phosphate ($Na_2H_2PO_4$) at concentrations of 5 g/L and 2.5 g/L, respectively.

In treating beehives, phages are included in the sugar-water feed either given to the bees as food or sprayed directly on hive frames with or without bees or larvae present. Phages may be delivered or sent in a concentrate and have the beekeeper make a dilution of the phage concentration in an appropriate amount of their sugar-water feed (roughly 1.5 cups total per hive). In the lab, a 20 mL dose of phages was diluted with 320 mL of solution containing 541 g table sugar (approximately a 2:1 sugar-water mixture, which is the typical sugar-water feed given to bees by beekeepers). The dilution of concentrated phages into sugar-water reduced the PBRI concentration, such that the final concentration of NaCl and $Na_2H_2PO_4$ is at or less than 294 μg/mL and 147 μg/mL, respectively. The beekeeper treated a hive with the sugar water containing phages by putting the solution in the hive feeding-trough or by using a sprayer to spray down racks in the hive. The prophylactic treatment is recommended once every week for 3 weeks for a total of 3 treatments, to be given in place of the antibiotic prophylactic treatments during spring and fall each year. For treatment of hives with an active infection, a total of 4 treatments is preferred. The sugary phage solution is eaten by worker bees and fed to larvae by the workers, which provides the way for phages to infect live bacteria directly in the bee gut.

Data has been obtained to demonstrate the safety and efficacy of the disclosed phage treatments in honeybees. These data include the study of phages that infect two bacterial targets: *Paenibacillus larvae* (PL) and *Brevibacillus laterosporus* (BL). The PL bacterium is the causative agent of AFB. PL phages directly kill active PL, thereby helping to clear the infection in larvae and on racks in the hive after larval death when the PL bacteria are consuming the dead larvae. PL bacteria are in spore form until a larvae receives it. Therefore, adult bees can ingest PL spores, do not become ill, but instead can deliver the spores to the vulnerable larvae when feeding them by regurgitating the contents of their first stomach. As a natural control measure for the disease, adult bees have fibers in the honey stomach (i.e., the first stomach) that can push spores to the second stomach and the adult will deposit the spores outside of the hive in their excrement.

AFB occurs when the load of spores in the adult bee is too high for the honey stomach fibers to move all of the spores down to the lower digestive tract and spores are delivered to the larvae. Since PL is in spore form in the adult bee, PL phage consumption by the adult bee may result in PL phage binding to the spores, but the phages cannot actively infect and kill the spore until it is delivered inside a larval gut to germinate into an actively growing bacterium. BL bacteria, while not the causative agent of AFB, are commonly found in combination with PL bacteria and can actively grow in the adult bee. The disclosure contemplates treating AFB by causing, when BL phages infect BL bacteria, the BL bacteria to release an antibacterial component that kill or prevent neighboring PL bacteria from growing and that appears to alter the activity of the gut in the adult bee to improve clearance of PL bacteria. Data show that the treatment of AFB by BL phages ultimately functions to clear a PL infection and can consequently effectively be used as a prophylactic treatment against AFB. The phage products disclosed and utilized herein will therefore include the choice of cocktails with PL phages or BL phages alone, or a combined cocktail of PL and BL phages so that the infection can be cleared both at the level of the larvae and the adult bee.

Data on the safety of phages used in newly installed and well-established honeybee colonies has been obtained. The data indicate that phage treatments as disclosed herein, as well as at 3-times and 5-times more concentrated doses, given repetitively over a 9-week period do not affect the colony expansion rate or bee death rate compared to controls. The data further show that hives treated prophylactically with phages have a significantly higher number of healthy hives compared to hives treated prophylactically with antibiotics. Treatment of naturally infected beehives indicate that BL phages can clear AFB at a 75% success rate and treatment with PL phages in our studies to this point have a 100% success rate of clearing active AFB infection.

The phage treatment disclosed herein has obtained unexpectedly good results and is a spectacular option for beekeepers to improve the health of their bees, prevent AFB outbreaks, and treat hives that are sick with AFB while also reducing the level of antibiotic exposure to the food supply and to the environment.

Overview

Pharmacological Category: Antimicrobial Phage therapy
Dosage Form(s): liquid
Amount of Active ingredient(s): 20 mL per treatment. $2\times10^{9}$-$2\times10^{10}$ phage per treatment.
How Supplied: Plastic Bottle
How Dispensed: Over-the-counter (OTC)
Dosage(s): Curative: 20 mL per hive every 3 days for 4 treatments.
Preventative: 20 mL per hive Weekly for 3 weeks.
Route(s) of Administration: Oral—20 mL mixed with 50 mL of 2:1 sugar water.
Preventative: spray onto the hive. Active: add to feeder.
Species/Class(es): Honeybees
Indication(s): For the control of American Foulbrood (*Paenibacillus larvae*) in honeybees.
Effect(s) of Supplement: This phage therapy provides an organic treatment option to killing American Foulbrood.

BL Phage AFB Treatment Data

Treatment Study: This study provides disclosure relating to the potential effectiveness of using phages, such as BL phages, to combat diseases and bacterial infections, such as PL infection causing AFB in honeybees.

For purposes of the disclosure, experimental infection of beehives was never performed or done. Instead, the treatment of the disclosure relied on contact from beekeepers experiencing a naturally-occurring AFB infection to provide test subjects. Throughout the disclosure, beekeepers were provided the choice of attempting curative treatment using either antibiotics or phages, or to destroy the infected beehives by burning. If a curative treatment was attempted and the hives did not experience recovery within two weeks, the infected beehives were destroyed by burning.

This curative-treatment study used BL phages with 12 infected beehives, which were treated with a cocktail of three BL phages.

Study Design: Test animals—Twelve colonies (hives) of honeybees (*Apis mellifera*) were previously established in one apiary. Originally all of the hives were sick with American Foulbrood. All 12 sick hives were treated with BL phage cocktail and observed after 14 days.

Route of administration: Oral.

Treatment: BL phage cocktail diluted in sugar water.

Objective and design: The objective was to determine the effectiveness of BL phages in curing AFB. Twelve beehives were confirmed by visual inspection as AFB-infected hives in an apiary of about 40 beehives. After visual inspection of all the beehives, the beekeeper moved all beehives lacking signs of AFB to a new location away from the 12 infected beehives and requested that a curative treatment using phages be attempted on the 12 sick hives. All 40 beehives were inspected after two weeks as the curative-treatment study endpoint. Infected hives that recovered after treatment were followed for 9 months, with some retreatments as described in the post-treatment longitudinal study data.

Samples of partially disintegrated larvae were taken from the hive to confirm the presence of *Paenibacillus larvae*. Hives were treated three times by spraying each rack on both sides. The hives were inspected two weeks after the first treatment and pictures of each frame were taken as a record of the data. After the study, the beekeeper reported the success of rescued hives to over-winter, as well as a report of any spring recurrence of the infection. Hives were monitored and treated during spring and summer upon recurrent infection.

Results:

Negative control hives: 2 of 28 healthy hives were infected with AFB. 2 of 2 infected, untreated hives died.

Approximately 28 hives were removed from the apiary where the 12 diseased hives were found. These 28 hives were inspected at the beginning of the study and deemed healthy because they lacked signs of AFB infection. After two weeks, the beekeeper inspected the 28 hives again and reported that two of the hives must have been infected with AFB in too early of a stage to have observed it at the beginning of the study. These two hives now had severe cases of AFB and were too far diseased at that point to attempt any treatment. The two sick hives were destroyed by burning. The remaining 26 hives appeared healthy and were preemptively treated with antibiotics. No further problems were reported.

Infected beehives treated with phages: 9 of 12 infected hives recovered with BL phage treatment. The 12 AFB-infected beehives were treated with BL phages the first day of the study. The hives were then treated two additional times with two or three days between treatments. The 12 hives were inspected at day 14 of the study. Of the 12 sick hives treated with BL phages, 9 hives appeared to be fully recovered, 3 hives died and their boxes were destroyed by burning. This is a 75% success rate. The decomposing larvae samples taken from the hives during the infection yielded PCR results positive for PL; however, BL was not identified in any larval sample. These results indicate that the AFB infection was caused by a PL infection as would be expected, and further that BL phage treatment has the ability to help clear PL infections despite that it does not infect PL.

Post-treatment overwintering data: 5 of 8 recovered hives were able to overwinter. Treatment of the beehives occurred immediately before the winter set in. Of the 9 recovered hives entering winter, 5 hives survived until spring, 4 hives died, 3 of which froze to death with the colony bees left dead in place in the hive and 1 hive was destroyed by vandals observable by extensive damage to the hive walls with shotgun holes and shells were found at the site. The vandalized hive lacked surviving or dead bees, indicating that the bees were alive when shot and likely abandoned the hive at that time. With 5 of 9 hives surviving, the overwinter survival rate would be 55%, which is lower than the national average overwinter survival rate of 76.8% for that winter. Overwinter survival rates in the USA range from 64.0%-78.1% as surveyed for winters between 2006-2015. Since it is unknown as to whether the vandalized hive would have or did survive the winter, if the remaining 8 hives were considered the sample number for overwinter survival, then these recovered beehives experienced 62.5% overwinter survival, which is just below the lowest in the national average range of overwinter survival statistics. If the vandalized hive survived winter, the rate would have been 75%, within the normal range of overwinter survival for honeybees in the USA.

Post-treatment longitudinal study (spring and summer post-treatment): 5 hives receive periodic BL phage treatment to prevent recurrent AFB. In March, all 5 surviving hives had new brood with no signs of AFB infection. In April, one of the 5 surviving hives experienced an AFB infection and that hive was able to recover after another treatment of BL phages but experienced periodic recurrent AFB infections, treatable each time with reapplication of BL phages. At each time of recurrence, all 5 hives in the apiary were treated with BL phages. After a few weeks, the first hive and a second hive experienced mild AFB symptoms which were again treatable with BL phages to remove signs within a week of the treatment. All 5 hives were given phage treatment every three or four weeks to prevent recurrence of AFB. The hives were destroyed mid-summer to end the longitudinal study. The recurrent infections indicated that PL spores remained in the hives after the BL treatment in a similar manner as occurs after antibiotic treatments of AFB-infected hives.

No adverse reactions were observed in this study.

Figure 4:
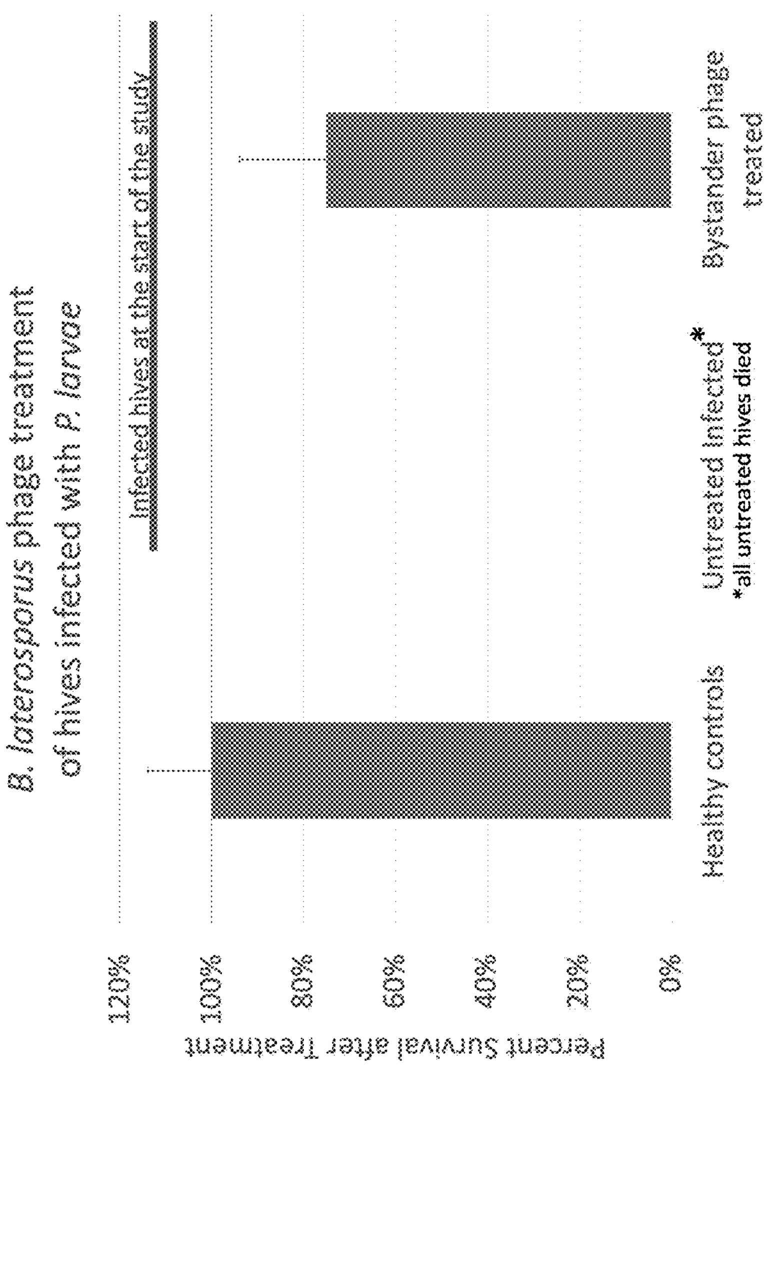
FIG. 4 is a graph illustrating the results of *Brevibacillus laterosporus* phage treatment on infected beehives in accordance with the teachings and principles of the disclosure.

Conclusions: The BL phage treatment demonstrated a 75% success rate in recovering actively-infected beehives from AFB (as illustrated in FIG. 4). After BL phage treatment, the recovered hives were sufficiently healthy to overwinter, albeit at a slightly lower rate than the national overwinter average. This particular AFB outbreak was sufficiently virulent to cause complete collapse of a beehive, as observed in the two hives that were misidentified in the healthy control group that must have been infected without noticing at the start of the study. The virulence of the bacteria is evident by the loss of these two colonies within two weeks of the study start time and during the same time period that the diseased colonies completely recovered after BL phage treatments. AFB-diseased beehives treated with BL phages retain bacterial spores from the infection that required ongoing maintenance to prevent recurrent AFB the following spring and summer.

PL Phage AFB Prevention and Curative Treatment Data

Treatment Study: This study provides disclosure relating to the potential effectiveness of using phages, such as PL phages, to combat diseases and bacterial infections, such as PL infection causing AFB in honeybees.

For purposes of the disclosure, experimental infection of beehives was never performed or done. Instead, the treatment of the disclosure relied on contact from beekeepers experiencing a naturally-occurring AFB infection to provide test subjects. Throughout the disclosure, beekeepers were provided the choice of attempting curative treatment using either antibiotics or phages, or to destroy the infected beehives by burning. If a curative treatment was attempted and the hives did not experience recovery within two weeks, the infected beehives were destroyed by burning.

This combined at-risk preventative and curative-treatment study using PL phages occurred when 11 beehives were observed and treated with PL phages in an apiary where one beehive was initially infected.

Study Design: Test animals—Eleven colonies (hives) of honeybees (*Apis mellifera*) were previously established in one apiary and experienced AFB in a single beehive. All 11 hives were included in the study as described in the experimental design.

Route of administration: Oral.

Treatment: PL phage cocktail diluted in sugar water.

Objective and design: This study included two objectives. First, Curative: The objective was to determine the effectiveness of PL phages in curing AFB using the spray method for phage treatment. Second, Preventative: The objective was to determine the effectiveness of PL phages to prevent the infection of healthy hives living in the same apiary as an AFB-infected beehive using the in-hive feeding trough method for phage treatment.

One beehive was confirmed by visual inspection as having an active AFB infection in an apiary of 11 beehives. The sick hive and 5 healthy hives were treated with PL phage cocktail, 5 healthy hives received no treatment as untreated healthy controls and all hives were observed at weeks two and four. At four weeks, all beehives, including newly-observed sick hives in the untreated control group, were treated again with PL phage cocktail and observed after two weeks later. Hives were managed normally and observed again at three months for signs of sickness. For all treatments, phages were diluted in 2:1 sugar water and the same volume of treatment was either sprayed on all racks in the hive (to treat sick beehives) or placed in the in-hive feeder (in healthy hives for preventative treatment).

Samples of partially disintegrated larvae were taken from the hive at the beginning of the study to confirm the presence of PL. Hives were treated three times by spraying each rack on both sides. For each observation time point, all the colonies were rated on a 0-3 scale based on a modification of the method proposed by Hitchcock et al. (1970). All the hives were examined and each of the frames were rated as follows:

0=no signs of disease

1=<10 cells per frame affected

2=11-100 cells per frame affected

3=>100 cells per frame affected

Results: Negative control hives: 4 of 5 healthy, untreated hives became infected with AFB. All 10 healthy hives were considered 'at risk' of contracting AFB due to the fact that one beehive in that apiary was found sick with the disease. These 10 hives were divided between the negative control group and the Preventative PL phage treatment group. Of the five healthy, untreated hives, four hives became sick with AFB within four weeks. Of these four fives, two of the hives scored 1 on the Hitchcock scale, one hive scored 3, and one hive collapsed completely with signs of severe AFB-diseased brood and very few bees. The collapsed hive was destroyed. This data indicates that 80% of 'at risk' untreated hives in this apiary contracted AFB. The three surviving diseased hives were then treated with PL phages.

Preventative PL phage treated hives: 5 of 5 healthy, PL-phage treated hives remained healthy. All 10 healthy hives were considered 'at risk' of contracting AFB, and the data from the negative control hives indicates that the risk of contracting AFB in that apiary was 80%. Of the five healthy hives that were treated with PL phages, all five were found healthy at week 4, which is the same week that the untreated control hives were found diseased. All preventative PL phage treated beehives remained healthy throughout the study.

Since the untreated control hives became sick after four weeks, it was decided that the five still-healthy hives in the preventative group, the one originally ill hive, and the one still-healthy untreated control hive were now at risk of contracting AFB from the newly-diseased hives, so all hives in the apiary were treated at 4 weeks. All seven hives that were healthy at week 4 remained healthy throughout the remainder of the study, indicating the PL phage treatment prevented AFB in at-risk hives, which is a 100% preventative rate from this study.

Curative PL phage treated hives: 4 of 4 AFB-disease hives fully recovered with PL phage treatment. At the beginning of the study, only one of the 11 hives had AFB, and it scored 2 on the Hitchcock scale. The decomposing larvae samples taken from the hive during the infection yielded PCR results positive for PL, the causative agent of AFB. This hive was treated with PL phages and fully recovered within two weeks. When the four negative control hives were found sick at week four, they scored an average of 2 on the Hitchcock scale. Since one hive was already decimated, the three surviving AFB-diseased hives were treated with PL phages and all three fully recovered within two weeks. These three hives, as well as the original sick hive indicate that 4 of the 4 curative PL phage treated hives recovered, which is a 100% recovery rate from this study.

Post-treatment longitudinal study (summer and fall post-treatment): 10 of 10 hives remained healthy after PL phage treatment and honey was harvested from all hives in fall. In fall, all 10 remaining hives in the apiary were healthy and lacked signs of AFB. Honey was harvested from all 10 hives. The hives were inspected again in October, prior to entering winter, and all 10 hives remained healthy and lacked any signs of AFB. Table 1 summarizes the data from this study.

TABLE 1

AFB disease in beehives at each time point in the PL phage treatment study.

| Hive Treatment Groups | Total # of hives | # of hives healthy:sick at day 0 | # of hives healthy:sick at week 2 | # of hives healthy:sick at week 4 | # of hives healthy:sick at week 6 | # of hives healthy:sick (October) |
|---|---|---|---|---|---|---|
| Original AFB-diseased hive | 1 | 0:1* | 1:0 | 1:0* | 1:0 | 1:0 |
| At-risk healthy hives, PL phage treated | 5 | 5:0* | 5:0 | 5:0* | 5:0 | 5:0 |
| At-risk healthy hives, untreated | 5 | 5:0 | 5:0 | 1:4*† | 4:0 | 4:0 |

*PL phage treatments were given at this time.
†One of the four diseased hives died of AFB.

Referring to FIG. 1, it will be appreciated that the results of PL phage treatment on infected and at-risk beehives is illustrated. Phage treatments were administered on day 0 and at week 4.

Adverse Reaction: No adverse reactions were observed in this study.

Conclusion: This study demonstrated the effectiveness of PL phages as a curative treatment of active AFB infection and as a preventative treatment in at-risk beehives.

PL Phage AFB Prevention and Safety in Healthy, not-at-Risk Beehives

Treatment Study: This study provides disclosure relating to the potential effectiveness of using phages, such as PL phages, when treating healthy beehives that are not at risk for AFB.

This combined not-at-risk preventative and safety treatment study using PL phages occurred when 96 beehives were observed and assigned to one of three groups to either be control hives, hives treated preventative PL phages, or hives treated with preventative Tylan antibiotic. None of the beehives exhibited signs of AFB at the beginning of the study, and no AFB was observed throughout the study.

Study Design: Test animals—A total of 96 colonies (hives) of honeybees (*Apis mellifera*) were previously established in two near-by apiaries. Each of the colonies had to meet the following four criteria: a viable laying queen, contain approximately 40,000 or more adult worker bees, have uncapped brood, and have no visible signs of American Foulbrood. All 96 hives met the criteria and were included in the study.

Route of administration: Oral.

Treatment: PL phage cocktail diluted in sugar water.

Objective and design: The objective was to determine the comparative health of beehives left without a treatment to hives prophylactically treated with PL phages or Tylan antibiotic for the prevention of AFB in a longitudinal study.

All 96 beehives were inspected in spring and fall using a 3-brood rack approach, wherein observation of three full brood racks constituted a complete inspection to look for AFB. Hives that looked unusual were inspected beyond the 3-brood racks. For each hive observation upon signs of AFB, the colonies were to be rated on a 0-3 scale based on a modification of the method proposed by Hitchcock et al. (1970). Frames were rated as follows:

0=no signs of disease
1=<10 cells per frame affected
2=11-100 cells per frame affected
3=>100 cells per frame affected For each hive inspected, other observations were also noted, such as signs of chalkbrood, European Foulbrood (EFB), apparent mite infestation, queen health (based on laying patterns, etc.), other obvious disorders, and any colony loss. Table 2 summarizes the treatment groups.

TABLE 2

Hives at each apiary were assigned to one of three groups to divide the 96 hives equally between treatments.

| Group | Apiary 1 | Apiary 2 | Total # of Hives | Treatment Regimen |
|---|---|---|---|---|
| Control | 16 | 16 | 32 | Three treatments of 2:1 sugar water in feeding trough. |
| Tylan | 16 | 16 | 32 | Three treatments of Tylan in powdered sugar in early spring and in early fall. |
| PL Phages | 16 | 16 | 32 | Three treatments of PL Phages in 2:1 sugar water in late spring and in early fall in feeding trough*. |

*Some hives received spring PL phage treatment as a spray of instead of in the trough but the volume and contents of the treatments were identical for all hives.

Results: AFB was not detected in any hive in any group throughout the study. Fall data represents the number of healthy hives and “diseased” or dead hives. For this study, a hive was counted as “diseased” if it had chalkbrood, had European Foulbrood, or struggled to thrive. None of the dead hives died from AFB.

Control group after fall inspection: Of 32 hives, 3 were diseased/died and 29 remained healthy. The control group exhibited a 90.6% positive health survival rate for the duration of the spring, summer and fall.

Tylan antibiotic group after fall inspection: Of 32 hives, 12 were diseased/died and 20 remained healthy. The Tylan antibiotic group exhibited a 62.5% positive health survival rate. This is statistically significantly different ($p=0.0146$) from the control group’s health using a two-tailed Fisher’s exact test for 2×2 contingency tables with $\alpha=0.05$. Health issues included European Foulbrood (EFB), Chalk Larvae, and hive death of unknown causes.

PL phage group after fall inspection: Of 32 hives, 6 were diseased/died and 26 remained healthy. The PL phage treated group exhibited an 81.3% positive health survival rate. This is not statistically significantly different ($p=0.4741$) from the control group’s health using a two-tailed Fisher’s exact test for 2×2 contingency tables with $\alpha=0.05$.

TABLE 3

Results of hive health study comparing antibiotics to PL phage as prophylactic treatments.

| Group | Diseased or Dead Hives | Diseased or Dead Hives | % Healthy Hives |
|---|---|---|---|
| Control | 32 | 3 | 90.6% |
| Tylan | 32 | 12 | 62.5% |
| PL Phages | 32 | 6 | 81.3% |

Longitudinal study (overwinter and next spring/fall treatments): These 96 hives are continuing with the prophylactic treatment of the Tylan and PL phage groups again as well as the untreated control group. It is possible that the untreated control group will experience a natural AFB outbreak at some point in the future, which will help us better understand the ability of the PL phages to prevent infection in comparison to the Tylan treated group. Even without an AFB outbreak, following the health of these hives better helps us understand any subtle health issues that might occur from the PL phage preventative treatment.

Adverse Reaction: No adverse reactions were observed in this study.

Conclusions: This study provides evidence that prophylactic Tylan treatment is detrimental to the overall health of otherwise healthy honeybees. The bees receiving Tylan had a statistically higher incident of disease and/or death of the hive. The health of the bees receiving phage treatment was not statistically different than the health of the untreated control bees.

BL Phage Safety Study in Healthy, not-at-Risk Beehives

Treatment Study: This study provides disclosure relating to the safety of using phages, such as BL phages, when treating healthy beehives that are not at risk for AFB.

This study was conducted with 12 healthy, not-at-risk beehives, which were divided into a control group and a treatment group to receive treatments of BL phages. Hives were observed for population expansion. None of the beehives exhibited signs of AFB at the beginning of the study, and no AFB was observed throughout the study.

Study Design: Test animals—A total of 12 colonies (hives) of honeybees (*Apis mellifera*) were installed from purchased packages into new hives. Hives were inspected weekly for the population size before and after receiving treatments.

Route of administration: Oral.

Treatment: PL phage cocktail diluted in sugar water.

Objective and design: The objective was to determine the comparative population growth of bees left without a treatment to hives or prophylactically treated with BL phages.

Population growth was followed in each hive based on “bee spaces” of bees. With racks in place, a full “bee space” occurs when the space between the racks is fully crowded by bees. The phage treatment began once all hives had achieved at least four bee spaces. Half of the hives were treated with BL phages by spray method, the other half were left untreated.

Results: Hive establishment. Packages of bees were installed into new hives in May and inspected weekly. Populations maintained approximately just below four bee spaces of bees throughout May and June and began expanding beyond four bee spaces at the beginning of July.

Population expansion after BL phage treatment. Bee expansion occurred in both the control hives and the BL phage treated hives between July and September. The hives expanded at the same rate over time. The data does not yield any statistical difference between the phage treated hives and the control hives in the population of bees observed in a repeated measures, mixed procedure, two-tailed statistical analysis of the number of bee-spaces between racks in the treated and control hives over a 17-week period using an alpha level $\alpha=0.05$ (P-value of 0.1104).

Figure 2:
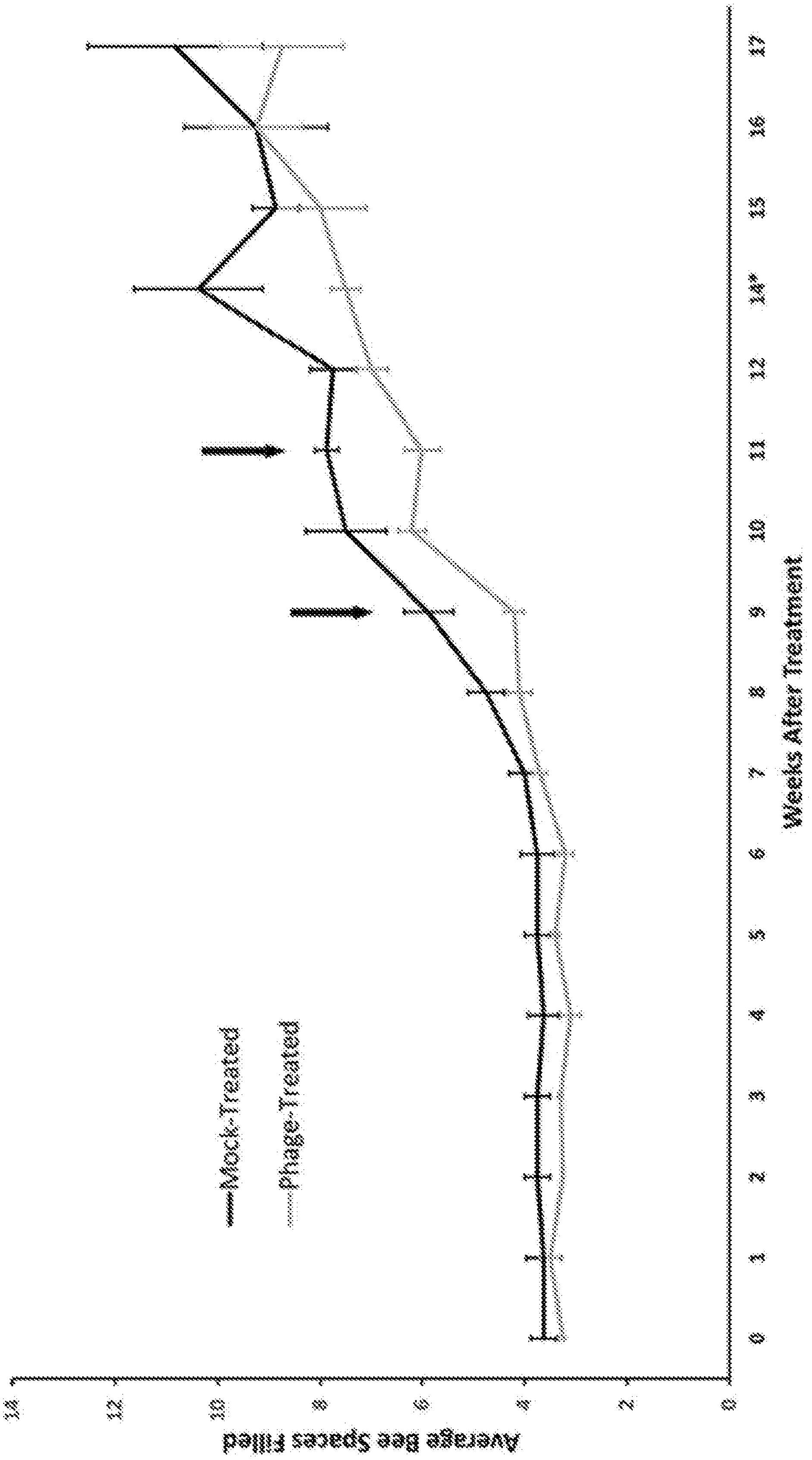
FIG. 2 is a graph illustrating bee density (measured in bee spaces) over time in control hives and *Brevibacillus laterosporus* phage-treated hives in accordance with the teachings and principles of the disclosure.

Referring now to FIG. 2, there is illustrated a graph showing bee density (measured in bee spaces) over time in control hives and BL phage-treated hives. Black arrows indicate treatment dates.

Conclusions: BL phage treatment does not alter the expansion of a population of bees in newly established beehives. This data is useful to show that, while above reports confirm that BL phages induce killing of non-target *Paenibacillus larvae* in infected hives, they do not alter the ability for population expansion in healthy bees.

PL Phage Safety Study in Healthy, not-at-Risk Beehives

Treatment Study: This study provides disclosure relating to the safety of using phages, such as PL phages, when treating healthy beehives that are not at risk for AFB.

This treatment study using PL phages occurred from June through August when 24 beehives were observed and assigned to one of four groups: control hives, and hives treated with PL phages at recommended treatment concentrations, or PL phages at three times (3×) and five times (5×) the recommended treatment concentrations. Dead bees were collected and counted each week to determine whether an increased concentration of phages could produce any increase in bee death. None of the beehives exhibited signs of AFB at the beginning of the study, and no AFB was observed throughout the study.

Study Design: Test animals—A total of 24 colonies (hives) of honeybees (*Apis mellifera*) were previously established in three near-by apiaries. Each of the colonies had to meet the following four criteria: a viable laying queen, contain approximately 40,000 or more adult worker bees, have uncapped brood, and have no visible signs of American Foulbrood. All 24 hives met the criteria and were included in the study.

Route of administration: Oral.

Treatment: PL phage cocktail diluted in sugar water.

Objective and design: The objective was to determine the comparative health of beehives left without a treatment to hives treated with PL phages at higher-than-recommended doses for the prevention of AFB in a study meant to observe bee death rates.

Hives treated with PL phages received either the standard dose of phages or a 3× or 5× concentration of phages, with each solution delivered in 2:1 sugar water. The control group received 2:1 sugar water without phages. The sugar water was delivered in in-hive feeders and the treatment was given once per week for nine weeks, for a total of nine treatments, which is three times the number of treatments recommended for a hive each spring or fall. This treatment delivers 15 times the dose of phages in the highest treatment group in order to observe whether this treatment alters the death of bees in a hive. Table 4 summarizes the treatment groups. Each of the three apiaries housed eight beehives. For each apiary, hives were randomly assigned the treatment regimen to receive. Therefore, each apiary had two hives assigned for each treatment group for a total of the four treatment groups between the eight hives at each location.

A portion of house bees in a colony carry dead bee bodies out of the hive and drop the bodies from the front porch of the hive as a part of the house bee cleaning duties. A 'dead-bee trap' was installed beneath each beehive to capture bee bodies tossed from the hive. Contents of traps were collected weekly and bee bodies counted as a measure of bee death over time.

TABLE 4

Hives at each apiary were assigned to one of four groups to divide the 24 hives equally between treatments.

| Group | # of Hives | Treatment regimen |
|---|---|---|
| Control | 6 | Each colony received 1 liter of 2:1 sugar water. |
| 1x | 6 | Each colony received 10 mL of treatment of PL phages in a liter of 2:1 sugar water. |
| 3X | 6 | Each colony received 30 mL of treatment of PL phages in a liter of 2:1 sugar water. |
| 5X | 6 | Each colony received 50 mL of treatment of PL phages in a liter of 2:1 sugar water. |

Results: All hives experienced a decline in bee death over the summer months, indicating strong hive health. No statistical difference (P-value of 0.639) was observed in bee deaths between the different phage treated hive concentrations and the control samples in a repeated measures, mixed-procedure, two-tailed statistical analysis of dead bees collected from the treated and control hives over a nine-week period with $\alpha=0.05$. One hive in the 3× group was observed to be an outlier and exhibited higher death rates than all other hives. The results of data comparison between groups remained insignificant whether this group was included in the statistical analysis or not.

Figure 3:
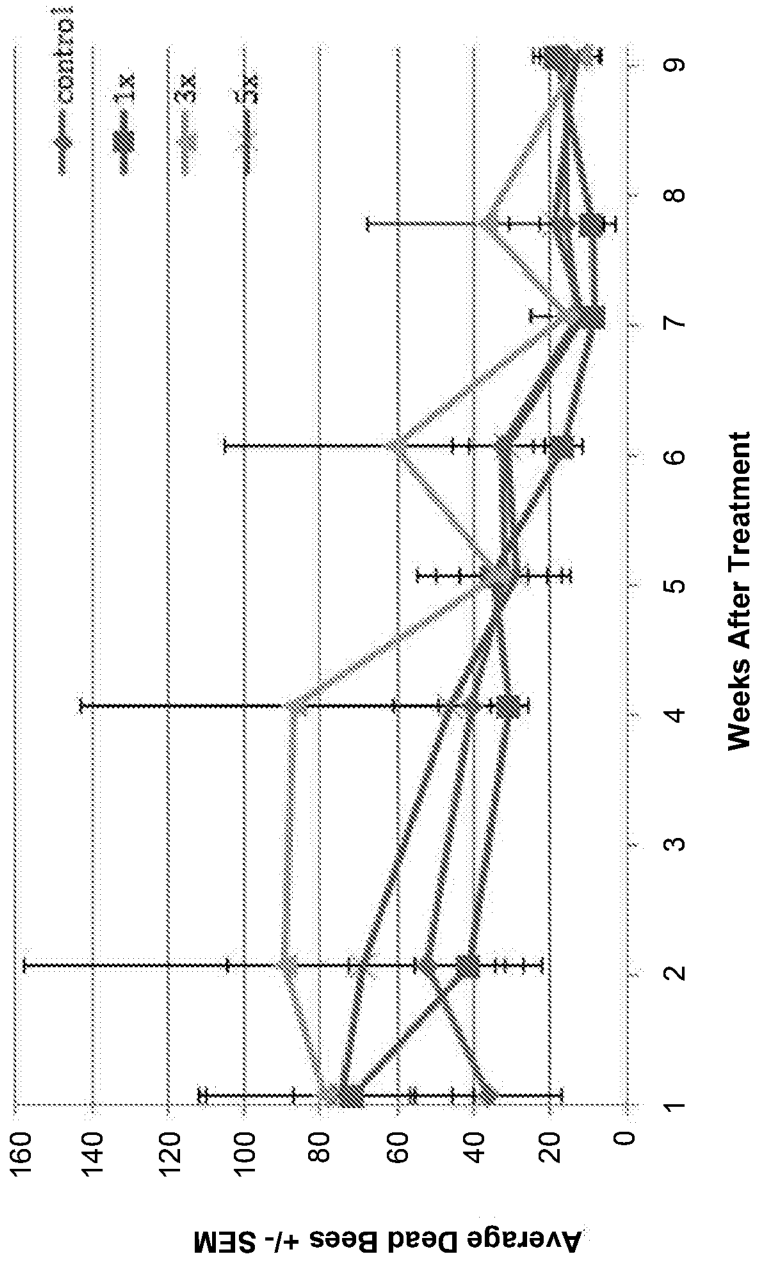
FIG. 3 is a graph illustrating the average bee death over time in control and *P. larvae* phage-overdosed beehives in accordance with the teachings and principles of the disclosure.

Referring now to FIG. 3, there is illustrated a graph showing average bee death over time in control and PL phage-overdosed beehives.

Conclusions: Even at the highest exposure in this study, the PL phage treatment did not produce any statistical difference in bee death rates compared to that of untreated hives or hives treated. The study provides evidence of the safety of phage-laden feed ingested by honeybees.

Experiments and studies have been performed on the cross-infection ability of *Brevibacillus laterosporus* phages and *Paenibacillus larvae* phages. Concentration of Phage in a normal Dose: $2\times10^{9}$-$2\times10^{10}$ phage per treatment. Broth concentration in treatment: 20 mL per dose. Dangerous chemical amount in a treatment (1 liter): 426 μmol NaCl per dose; 88 μmol $Na_2H_2PO_4$ per dose.

Preventative Treatment:

In a liter: 0.02 mL of broth per mL 2:1 sugar water.

Dangerous chemicals present in hive: 426 μM NaCl; 88 μM $Na_2H_2PO_4$

In a gallon: 0.00528 mL of broth per mL of 2:1 sugar water.

112.54 μM NaCl; 23.2 μM $Na_2H_2PO_4$

Active Infection Treatment:

In 300 mL: 0.0667 mL of broth per mL of 2:1 sugar water.

1.42 mM NaCl; 293 μM $Na_2H_2PO_4$

Kits, Systems, and Methods for Treating or Preventing Bacterial Infections in Non-Human Animals Embodiments of the present disclosure can include kits, systems, and methods for treating or preventing an infection caused by a primary bacterium or four use in reducing or preventing the overpopulation of the primary bacterium. Kits disclosed herein can be implemented in an exemplary method including the act of administering a bacteriophage tropic for a bystander bacterium wherein the bystander bacterium has a genomically-encoded bacteriotoxin that is expressed upon infection by the bacteriophage and is specific for at least the primary bacterium. In some instances, the act of administering the bacteriophage tropic for the bystander bacterium comprises administering the bacteriophage to a non-human animal associated with the primary bacterium, preferably a non-mammalian animal associated with (e.g., infected by) the primary bacterium.

In one aspect, the disclosed kits, systems, and methods can be applied to the treatment and/or prevention of bovine mastitis. Current practices in managing bovine mastitis include managing milk production and inducing a rapid "dry period"—the two months before a cow will give birth to the next calf. During the dry period, the cow will have increased immune response within the teat canal in order to remove any bacteria that might be retained. Nevertheless, the cow is at the highest risk for developing mastitis during the dry period and common practice is to administer intra-udder injections of prophylactic antibiotics.

Instead of using an intra-udder injection of antibiotics and risking antibiotic resistant strains of *Staphylococcus aureus*, the causative agent of mastitis, and/or potentially tainting cows' milk with antibiotics, cows can be treated using the bystander phage therapy disclosed herein. In one aspect, kits of the present disclosure include kits for use in the treatment or prevention of mastitis in cows or for use in reducing or preventing overpopulation of *S. aureus*. The kit can include one or more bacteriophage tropic for a bystander bacterium having a genomically-encoded bacteriotoxin specific for at least *S. aureus*. In one embodiment, the one or more bystander bacterium includes one or more commensal bacterium of the cow teat, such as *Staphylococcus auricularis, Staphylococcus devriesei, Staphylococcus arlettae, Streptococcus bovis, Streptococcus equinus, Clavibacter michiganensis, Coprococcus catus*, or *Arthrobacter gandavensis*, and/or one or more bacterium found in raw milk, which includes, for example, *Enterococcus* sp., *Pediococcus* sp., *Enterobacter* sp., *Pantoea* sp., and *Aerococcus* sp. Regardless of source, the selected one or more bystander bacterium includes a genomically-encoded bacteriotoxin that is expressed upon infection by the phage and which targets at least *S. aureus.*

In some aspects, the bacteriophage tropic for the foregoing bystander bacteria include phages such as *Clavibacter* phages CMP1, CN1A, CN77, *Pediococcus* phages cLP1, cLP2, *Streptococcus equinus* phages Javan 199-219, *Enterococcus* phages, *Enterobacter* phages, *Pantoea* phages, *Aerococcus* phage vB_AviM_AVP, and/or *Staphylococcus* phages. When bystander phages are included with the bystander bacteria, the phages infect the bacteria and the bacteria begin to release stress factors, including antimicrobials specific to maintaining commensal status in the cow teat canal. In some embodiments, stress factors from the resident commensal bacteria may also signal other resident commensals to begin combatting the undesired bacteria (e.g., by secreting their own bacteriotoxins).

Mastitis affects other domesticated animals used for milk production, including, for example, goats and sheep. The most severe mastitis in goats is caused by *S. aureus*, and similar to cows, goats can be treated using bystander phage therapies disclosed herein. In one aspect, kits of the present disclosure include kits for use in the treatment or prevention of mastitis in goats or for use in reducing or preventing overpopulation of *S. aureus*. The kit can include one or more bacteriophage tropic for a bystander bacterium having a genomically-encoded bacteriotoxin specific for at least *S. aureus*. In one embodiment, the one or more bystander bacterium includes one or more commensal bacterium of the goat udders and/or those bacteria commonly found in goat's milk, such as *Micrococcus luteus, Bacillus cereus, Lactobacillus lactis, Escherichia coli, Shigella flexneri, Enterobacter cloacae*, and *Klebsiella pneumoniae*. Regardless of source, the selected one or more bystander bacterium includes a genomically-encoded bacteriotoxin (e.g., bacteriocin) that can be induced by the bystander phage specific to the bystander bacteria and that targets at least *S. aureus.*

Mastitis in sheep is also caused by *S. aureus* and can be treated in the same or similar manner as described above with respect to goats.

Colibacillosis is a economically important disease in poultry such as chickens and turkeys. It is caused by strains of Avian Pathogenic *E. coli* (APEC), typically in an opportunistic fashion after a bird has suffered from another infection such as a bronchitis-causing virus or mycoplasmosis, and results in respiratory, reproductive, and intestinal problems.

Currently, colibacillosis is treated using antibiotics. However, in one aspect, kits, compositions, and methods of the present disclosure can be implemented for use in the treatment or prevention of colibacillosis in poultry or for use in reducing or preventing overpopulation of APEC, which can be associated with the poultry as a gut symbiont and opportunistic pathogen. An exemplary kit can include one or more bacteriophage tropic for a bystander bacterium having a genomically-encoded bacteriotoxin specific for at least one strain of APEC. In one embodiment, the one or more bystander bacterium includes one or more intestinal commensal bacterium within chickens and/or turkeys, such as *Micrococcus luteus, Bacillus cereus, Lactobacillus lactis, Escherichia coli, Shigella flexneri, Enterobacter cloacae*, and *Klebsiella pneumoniae*. Regardless of source, the selected one or more bystander bacterium includes a genomically-encoded bacteriotoxin (e.g., bacteriocin) that can be induced by the bystander phage specific to the bystander bacteria and that targets at least one strain of APEC to clear the invasive *E. coli.*

Potential bacterial infections in nursing pigs include those caused by *Clostridium difficile, C. perfringens*, and *E. coli.* In weanlings and older piglets, diarrheal diseases are typically caused by *E. coli, Brachyspira pilosicoli, Lawsonia intracellularis, Salmonella*, or *Brachyspira hyodysenteriae.* Historically, antibiotics are used to treat these infections, but bystander phages can be used to treat these diseases. However, in one aspect, kits, compositions, and methods of the present disclosure can be implemented for use in the treatment or prevention of bacterial diarrheal diseases in pigs or for use in reducing or preventing overpopulation of a primary bacterium causative of or contributing to bacterial diarrheal diseases in pigs. An exemplary kit can include one or more bacteriophage tropic for one or more bystander bacterium having a genomically-encoded bacteriotoxin specific for at least one of *C. difficile, C. perfringens, E. coli, B. pilosicoli, L. intracellularis, Salmonella* sp., and/or *B. hyodysenteriae.*

In one embodiment, the one or more bystander bacterium includes one or more intestinal commensal bacterium within the pig intestinal microbiome, such as the RC9 gut group (e.g., includes the Rikenellaceae family and other core gut microbiota). Regardless of source, the selected one or more bystander bacterium includes a genomically-encoded bacteriotoxin that can be induced by the bystander phage specific to the bystander bacteria and that targets the primary bacterium, consisting of one or more of *C. difficile, C. perfringens, E. coli, B. pilosicoli, L. intracellularis, Salmonella* sp., and/or *B. hyodysenteriae*. It should be appreciated that nursing pigs may require a different bystander bacterium for use in the disclosed kits and/or methods than weanling or growing pigs due to differences in the core gut microbiome.

Horses are susceptible to digestive infections from enterotoxigenic *Escherichia coli, Salmonella* sp., *Rhodococcus equi, Actinobacillus equuli, Clostridium perfringens, C. difficile*, and *L. intracellularis*. Similar to those embodiments described above, horses can benefit from bystander phage therapies disclosed herein. For example, kits, compositions, and methods of the present disclosure can be implemented for use in the treatment or prevention of bacterial-caused digestive infections in horses or for use in reducing or preventing overpopulation of a primary bacterium causative of or contributing to bacterial-caused digestive infections in horses. An exemplary kit can include one or more bacteriophage tropic for one or more bystander bacterium having a genomically-encoded bacteriotoxin specific for at least one of enterotoxigenic *E. coli, Salmonella* sp., *R. equi, A. equuli, C. perfringens, C. difficile*, and *L. intracellularis*. Exemplary bystander bacteria can be selected from equine commensal gut microbes, preferably those of *Bacteroidetes* sp., *Firmicutes* sp., and *Fibrobactere* sp.

Kits, Systems, and Methods for Treating or Preventing Bacterial Infections in Plants Bacterial infections in plants can also be managed using bystander phage therapy. A variety of plant diseases are caused by bacterial infection. Direct phage therapy and other control methods have been attempted in nearly all of the following examples. Embodiments of the present disclosure replace direct phage therapy with bystander phage treatment. For plant applications, bystander bacteria can include soil and root bacteria such as *Azotobacter, Azospirillum, Clostridium, Rhizobium, Aerobacter, Streptomycetes*, and/or *Actinomycetes* species.

Bacterial wilt, for example, is caused by numerous species of the genera *Corynebacterium, Erwinia, Pseudomonas*, and *Xanthomonas*. Bacterial wilt induces stunting, wilting, and withering, starting usually with younger leaves. Stems, which often shrivel and wither, show discolored water-conducting tissue. A bacterial ooze is often evident when infected stems are cut and squeezed. Rapidly expanding, dark green, water-soaked areas or streaks may develop first in leaves. In tomatoes, bacteria wilt is caused by *Ralstonia solanacearum*. Bacterial wilt is generally managed by growing resistant varieties; planting disease-free materials in well-drained, fertile soil that is clean or sterilized; observing stringent sanitation including weed- and insect-control measures; and rotating susceptible crops. However, embodiments of the present disclosure can include a composition, kit, and/or method for treating bacterial wilt with bacteriophage tropic for a bystander bacterium having a genomically-encoded bacteriotoxin specific for the bacteria causing the bacterial wilt (e.g., *Ralstonia solanacearum* in tomatoes) and that is expressed upon infection with one or more complementary (narrowly tropic) phage.

Basal rot, also known as bulb rot, is a widespread disease that can infect all flower and crop bulbs and is caused by a variety of fungi and bacteria. Shoots fail to emerge or leaves are stunted and yellow to reddish or purplish; the leaves later wilt and die in plants infected with bacteria that cause basal rot. Potato rot, for example, is caused by *Pectobacterium carotovorum, Pectobacterium wasabiae*, and/or *Dickeya solani*. Embodiments of the present disclosure can include a composition, kit, and/or method for treating rot with bacteriophage tropic for a bystander bacterium having a genomically-encoded bacteriotoxin specific for the bacteria causing the rot (e.g., *Pectobacterium carotovorum, Pectobacterium wasabiae*, and/or *Dickeya solani* in potatoes) and that is expressed upon infection with one or more complementary (narrowly tropic) phage.

Blight is characterized as any of various plant diseases whose symptoms include sudden and severe yellowing, browning, spotting, withering, or dying of leaves, flowers, fruit, stems, or the entire plant. Most blights are caused by bacterial (or fungal) infestations, which usually attack the shoots and other young, rapidly growing tissues of a plant. Bacterial blights are most apt to occur under cool moist conditions, and most economically important plants are susceptible to one or more blights, including tomatoes, potatoes, and apples, as well as many ornamental species. Onion leaf blight, for example, is caused by *Xanthomonas axonopodis*, bacterial blight in leek plants is caused by *Pseudomonas syringae*, and fire blight in pears, apples, and other fruit (trees) is caused by *Erwinia amylovora.*

Bacterial blight first becomes evident as water-soaked streaks that spread from the leaf tips and margins, becoming larger and eventually releasing a milky ooze that dries into yellow droplets. Characteristic grayish white lesions then appear on the leaves, signaling the late stages of infection, when leaves dry out and die. In seedlings, the leaves dry out and wilt, a syndrome known as kresek. Infected seedlings usually are killed by bacterial blight within two to three weeks of being infected; adult plants may survive, though rice yield and quality are diminished.

Rice bacterial blight, also called bacterial blight of rice, is a deadly bacterial disease caused by *Xanthomonas oryzae* and is among the most destructive afflictions of cultivated rice. In severe epidemics, crop loss may be as high as 75%, and millions of hectares of rice are infected annually. The disease was first observed in 1884-85 in Kyushu, Japan, and the causal agent, the bacterium *Xanthomonas oryzae* pathovar *oryzae* (also referred to as Xoo), was identified in 1911, at that time having been named *Bacillus oryzae*. Thriving in warm, humid environments, bacterial blight has been observed in rice-growing regions of Asia, the western coast of Africa, Australia, Latin America, and the Caribbean.

Since rice paddies are flooded throughout most of the growing season, Xoo may easily spread among crops; bacteria travel through the water from infected plants to the roots and leaves of neighbouring rice plants. Wind and water may also help spread Xoo bacteria to other crops and rice paddies. Various mechanisms of disease, including quorum sensing and biofilm formation, have been observed in rice bacterial blight and Xoo. In addition to rice, Xoo may infect other plants, such as rice cut-grass (*Leersia oryzoides*), Chinese sprangletop (*Leptochloa chinensis*), and common grasses and weeds. In nongrowing seasons, Xoo may survive in rice seeds, straw, other living hosts, water, or, for brief periods, soil.

Common measures for controlling and preventing blights typically involve the destruction of the infected plant parts; use of disease-free seed or stock and resistant varieties; crop rotation; pruning and spacing of plants for better air circulation; controlling pests that carry the bacteria from plant to plant; avoidance of overhead watering and working among wet plants; and, where needed, the application of antibiotics. Proper sanitation is key to stop the spread of the infestation. For bacterial blights (e.g., fire blight), fixed copper or streptomycin is an effective antibiotic if applied weekly during damp weather when leaves and shoots are expanding.

Methods of controlling rice bacterial blight are limited in effectiveness. Chemical control has been largely ineffective in minimizing bacterial blight because of safety concerns, practicality, and bacterial resistance. Biological control methods, which rely on the use of bacterial antagonists of pathogens (disease-causing organisms), can reduce bacterial blight, though their use has been limited.

Embodiments of the present disclosure can include a composition, kit, and/or method for treating bacterial blight with bacteriophage tropic for a bystander bacterium having a genomically-encoded bacteriotoxin specific for the bacteria causing the blight (e.g., *Xanthomonas axonopodis* in onion (leaves), *Pseudomonas syringae* in leek plants, and *Erwinia amylovora* in pears, apples, and other fruit trees) and that is expressed upon infection with one or more complementary (narrowly tropic) phage.

Aster yellows is a plant disease caused by a phytoplasma bacterium and affects over 300 species of herbaceous broad-leafed plants. Aster yellows is found over much of the world wherever air temperatures do not persist much above 32° C. (90° F.). As its name implies, members of the family Asteraceae are vulnerable to infection, though the disease can also affect a variety of common vegetables, cereals, garden plants, and wild species. Typical symptoms include yellowing (chlorosis) of young shoots, stiff and erect bunchy growth, greenish and distorted or dwarfed flowers, and general stunting or dwarfing. The phytoplasma lives in the phloem of infected plants and is transmitted by leafhopper insects when they feed on an infected plant and then on a healthy one. No transmission occurs through leafhopper eggs or plant seed. The phytoplasma is perpetuated in overwintering weed and crop plants, in propagative parts (bulbs, corms, tubers), and in leafhoppers in mild climates. The phytoplasma is destroyed in plants and leafhoppers subjected to temperatures of 38 to 42° C. (100 to 108° F.) for two to three weeks; thus, aster yellows is rare or unknown in many tropical regions.

Though the disease is not lethal, aster yellows is controlled mainly by promptly removing diseased plants and all overwintering susceptible weeds. Spraying or dusting with a contact insecticide repulses the leafhopper carriers. Nevertheless, embodiments of the present disclosure can include a composition, kit, and/or method for treating aster yellows with bacteriophage tropic for a bystander bacterium having a genomically-encoded bacteriotoxin specific for the bacteria causing the aster yellows (e.g., phytoplasma bacterium) and that is expressed upon infection with one or more complementary (narrowly tropic) phage.

Canker is a plant disease caused by numerous species of bacteria, that occurs primarily on woody species. Symptoms include round-to-irregular sunken, swollen, flattened, cracked, discoloured, or dead areas on the stems (canes), twigs, limbs, or trunk. Cankers may enlarge and girdle a twig or branch, killing the foliage beyond it. They are most common on plants weakened by cold or drought stresses, insect injury, nutritional imbalances, nematodes, or root rot. In citrus fruit (trees), for example, *Xanthomonas axonopois* causes Asiatic citrus canker in grapefruit and Citrus Bacterial Spot in oranges.

Canker is generally controlled by removing diseased parts in dry weather; growing adapted or resistant varieties in warm well-drained fertile soil; avoiding overcrowding, overwatering, and mechanical wounds; treating bark and wood injuries promptly; controlling insect and rodent disease carriers; wrapping young trees to prevent sunscald; and keeping plants vigorous by the use of fertilizers. Nevertheless, embodiments of the present disclosure can include a composition, kit, and/or method for treating canker (e.g., Asiatic citrus canker in grapefruits, or Citrus Bacterial Spot in oranges) with bacteriophage tropic for a bystander bacterium having a genomically-encoded bacteriotoxin specific for the bacteria causing the canker (e.g., *Xanthomonas axonopois*) and that is expressed upon infection with one or more complementary (narrowly tropic) phage.

Crown gall is a plant disease caused by the bacterium *Agrobacterium tumefaciens* (synonym *Rhizobium radiobacter*). Thousands of plant species are susceptible. They include especially grape, members of the rose family (Rosaceae), shade and nut trees, many shrubs and vines, and perennial garden plants. Symptoms include roundish rough-surfaced galls (woody tumourlike growths), several centimeters or more in diameter, usually at or near the soil line, on a graft site or bud union, or on roots and lower stems. The galls are at first cream-colored or greenish and later turn brown or black. As the disease progresses, plants lose vigor and may eventually die.

Crown gall is generally controlled by using nursery stock free of suspicious bumps near the crown, former soil line, or graft union; practicing five-year rotation or avoiding replanting for that period; removing severely infected plants (including as many roots as possible); protecting against injury; keeping down weeds; controlling root-chewing insects and nematodes; cutting away large galls on trees; and disinfecting wounds. However, embodiments of the present disclosure can include a composition, kit, and/or method for treating crown gall with bacteriophage tropic for a bystander bacterium having a genomically-encoded bacteriotoxin specific for *Agrobacterium tumefaciens* (synonym *Rhizobium radiobacter*) and that is expressed upon infection with one or more complementary (narrowly tropic) phage.

Scab, in botany, is any of several bacterial (or fungal) plant diseases characterized by crustaceous lesions on fruits, tubers, leaves, or stems. The term is also used for the symptom of the disease. Scab often affects apples, crabapples, cereals, cucumbers, peaches, pecans, and potatoes. Leaves of affected plants may wither and drop early. Potatoes are especially susceptible to common scab. Potato scab is caused *Streptomyces* scabies (and related species), which spreads rapidly in dry alkaline soils.

Scab is generally controlled by avoiding the use of materials such as wood ash, fresh manure, and lime that will add alkalinity to the soil. Other disease-prevention methods include planting resistant varieties or disease-free seeds, tubers, and corms; destroying diseased parts; removing weeds; rotating vegetables and flowers; and regularly spraying plants with fungicides, if appropriate. However, embodiments of the present disclosure can include a composition, kit, and/or method for treating bacterial-pathogen-associated scab (e.g., potato scab) with bacteriophage tropic for a bystander bacterium having a genomically-encoded bacteriotoxin specific for *Streptomyces* scabies (or related species) and that is expressed upon infection with one or more complementary (narrowly tropic) phage.

Additional bacteria-related diseases include bacterial spot in potatoes (caused by *Xanthomonas campestris*), Pierce's Disease in grapes (caused by *Xylella fastidiosa*), and Brown Blotch Disease in mushrooms (caused by *Pseudomonas tolaasii*). Embodiments of the present disclosure can similarly include compositions, kits, and/or methods for treating any one or more of spot in potatoes, Pierce's Disease in grapes, and/or Brown Blotch Disease using bacteriophages tropic for one or more bystander bacterium having a genomically-encoded bacteriotoxin specific for a respective primary bacterium causative of and/or contributing to the pathology. As such, the respective genomically-encoded bacteriotoxin specific for a respective primary bacterium is expressed upon infection with one or more complementary (narrowly tropic) phage, as discussed herein.

Selection and Isolation of Bacteriophages and Bystander Bacteria

The process of isolating new bystander bacteriophages utilizes straightforward microbiology lab techniques and is typically not a limiting factor for application of the embodiments or claims described. Field samples can be taken from a common place where the bacteriophage and bacterial host are naturally found. For instance, in implementations of the disclosed treatment or prevention of honeybee infections, samples of bee debris or soil samples in the area of a beehive were gathered as the source of bystander-tropic bacteriophage. The field samples were incubated with the bystander host bacterium for culturing in a laboratory setting. Any present, naturally occurring phages were easily selected on plates. The phages were then systematically tested for induction of bystander bacteria toxin production, such as, for example, using similar methods and techniques known in the art for generating results similar to those depicted in FIGS. 5A-5C, which illustrates the results of a *B. latero-*

Figures 5A, 5B, 5C:
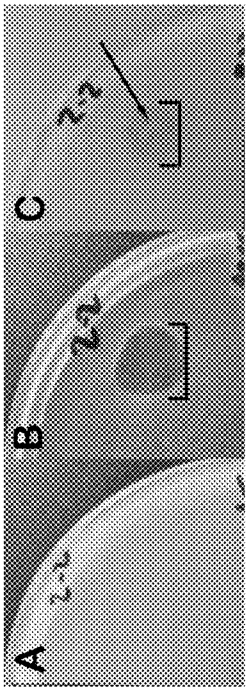
FIG. 5A-5C is a panel of images illustrating the results of *Brevibacillus laterosporus* phage induction of antimicrobial products. Drops of *B. laterosporus* phage lysate were placed and incubated for 24 h onto (i) a lawn of *Agrobacterium tumefaciens* that did not respond to the antimicrobial product or generate plaque clearings (as shown in FIG. 5A), (ii) a lawn of *P. larvae* that exhibited antimicrobial death (as shown in FIG. 5B), and (iii) a lawn of *B. laterosporus* strain BL2 that showed antimicrobial death as well as phage infection formation (as shown in FIG. 5C). The bracket illustrated in FIG. 5C indicates antimicrobial clearing, and the arrow indicates phage plaque formation.

*sporus* phage induction of antimicrobial products that kill *P. larvae* bacteria (e.g., as shown in FIG. 5B) in accordance with teachings and principles of the present disclosure. The process for isolation and testing can be accomplished, for example, in a matter of days or weeks.

In the above-mentioned example of kits and methods for treating or preventing mastitis in cattle, more than 566 known phages to commensal bacteria were isolated and characterized using microbiology lab techniques and samples from known sources of the bacterial hosts that could be used for bystander phage therapy. The examples listed of known bacterial hosts and phages do not limit the capability to obtain additional new isolations of bystander bacteriophages, but instead justify that capture of phages for the purposes of bystander phage treatment are not only possible, but relatively simple to do. For each of the aspects described (bacterial infections in insects, such as bees, or larger animals such as cows, goats, sheep, poultry, pigs, and horses, and bacterial infections in plants for wilt, rot, blight, cankers, gall, scab, etc.), bystander bacterial hosts are identifiable and phages have been and/or can be isolated using basic microbiology lab techniques Formulation and Dosage of Compositions As provided above, each of the disclosed compositions includes a pharmaceutically-acceptable carrier in addition to one or more bacteriophages having a narrow tropism for one or more bystander bacterium. As used herein the term "pharmaceutically acceptable" means a biologically compatible formulation, gaseous, liquid or solid, or mixture thereof, that is suitable for one or more routes of administration, in vivo delivery, or contact. A formulation is compatible in that it does not destroy activity of an active ingredient therein (e.g., the bacteriophage or bacteriophage cocktail) or induce adverse side effects that outweigh any prophylactic or therapeutic effect or benefit.

It should be appreciated that the disclosed compositions may contain one or more (pharmaceutically-acceptable) carriers or excipients. Pharmaceutically acceptable carriers and excipients (or the pharmaceutical acceptability thereof) are determined in part by the particular composition being administered, as well as by the particular method used to administer the composition. Accordingly, there exists a wide variety of suitable formulations of pharmaceutical compositions (see, e.g., Remington's Pharmaceutical Sciences, incorporated herein by reference). Suitable excipients may be or include carrier molecules and can include antioxidants such as ascorbic acid; chelating agents such as EDTA; carbohydrates such as dextrin, hydroxyalkylcellulose, hydroxyalkylmethylcellulose, and stearic acid; liquids such as oils, water, saline, glycerol and ethanol; wetting or emulsifying agents; pH buffering substances; and the like. Liposomes are also included within the definition of pharmaceutically acceptable excipients. Additional or alternative examples of carriers include silicon dioxide (silica, silica gel), carbohydrates or carbohydrate polymers (polysaccharides), cyclodextrins, starches, degraded starches (starch hydrolysates), chemically or physically modified starches, modified celluloses, gum arabic, ghatti gum, tragacanth, karaya, carrageenan, guar gum, locust bean gum, alginates, pectin, inulin or xanthan gum, or hydrolysates of maltodextrins. In various embodiments, the bacteriophage and/or bystander bacterium can be dispersed throughout the carrier. In various embodiments, the pharmaceutically acceptable excipient or carrier can be suitable for oral consumption.

The compositions described herein may be formulated in any form suitable for the intended method of administration. When intended for oral use, for example, tablets, troches, lozenges, aqueous or oil suspensions, non-aqueous solutions, dispersible powders or granules (including micronized particles or nanoparticles), emulsions, hard or soft capsules, syrups, or elixirs may be prepared. Orally consumable products can also include a semi-solid food, solid food, a semi-solid or solid spoonable food, confectionary, drink, or dairy product. The dairy product of various embodiments is ice cream, milk, milk powder, yogurt, kefir, or quark. Compositions intended for oral use may be prepared according to any method known to the art for the manufacture of pharmaceutical compositions, and such compositions may contain one or more agents including sweetening agents, flavoring agents, coloring agents, and preserving agents to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin, or acacia; and lubricating agents, such as magnesium stearate, stearic acid, or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents, such as sodium carboxymethylcellulose, methylcellulose, hydroxypropyl methylcellulose, sodium alginate, polyvinylpyrrolidone, gum tragacanth, gum acacia, dispersing, or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate); polysaccharides and polysaccharide-like compounds (e.g., dextran sulfate); glycoaminoglycans and glycosaminoglycan-like compounds (e.g., hyaluronic acid); and thickening agents, such as carbomer, beeswax, hard paraffin, or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters, or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol, or sucrose. Such formulations may also contain a demulcent, a preservative, a flavoring, or a coloring agent.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

It should be appreciated that the compositions and/or formulations disclosed herein contain a total amount of one or more bacteriophages and/or one or more bystander bacterium (collectively or individually) sufficient to achieve the intended effect (e.g., to treat or prevent an infection caused by a primary bacterium and/or to reduce the number and/or concentration of primary bacteria).

The compositions may, for convenience, be prepared or provided as a unit dosage form and can be packaged in unit dosage forms for ease of administration and uniformity of dosage. A "unit dosage form" as used herein refers to a physically discrete unit suited as unitary dosages for the subject to be treated. Each unit containing a predetermined quantity of the one or more bacteriophage and/or one or more bystander bacterium optionally in association with a pharmaceutically-acceptable carrier (e.g., excipient, diluent, vehicle or filling agent) which, when administered in one or more doses, is calculated to produce the desired effect (e.g., to treat or prevent an infection caused by a primary bacterium and/or to reduce the number and/or concentration of primary bacteria). Unit dosage forms can contain a daily dose or unit, daily sub-dose, or an appropriate fraction thereof, of an administered compound. Unit dosage forms also include, for example, capsules, troches, cachets, lozenges, tablets, ampules and vials, which may include a composition in a freeze-dried or lyophilized state. A sterile liquid carrier, for example, can be added prior to administration or delivery in vivo. Unit dosage forms additionally include, for example, ampules and vials with liquid compositions disposed therein. The individual unit dosage forms can be included in multi-dose kits or containers.

A dosage (or administration) of the composition can include one or more doses. A dose of the composition can include, for example, greater than or equal to $1\times10^4$ PFU/mL or PFU/mg of one or more bacteriophage, in accordance with one or more aspects or embodiments of the present disclosure. Alternative doses can include greater than or equal to $1\times10^5$, $1\times10^6$, $1\times10^7$, $1\times10^8$, $1\times10^9$, or $1\times10^{10}$ PFU/mL or PFU/mg of the one or more bacteriophage. Suitable dosage size or amounts can range from 1 μL to 500 mL or more (e.g., of fluid or semi-solid composition), 1 μg to 5000 mg or more (e.g., of solid or semi-solid composition), or another amount as known in the art.

A dosage (or administration) of the composition can additionally, or alternatively, include greater than or equal to $1\times10^4$ CFU/mL or CFU/mg of one or more bystander bacterium, in accordance with one or more aspects or embodiments of the present disclosure. Alternative doses can include greater than or equal to $1\times10^5$, $1\times10^6$, $1\times10^7$, $1\times10^8$, $1\times10^9$, or $1\times10^{10}$ CFU/mL or CFU/mg of the one or more bystander bacterium. Suitable dosage size or amounts can range from 1 μL to 500 mL or more (e.g., of fluid or semi-solid composition), 1 μg to 5000 mg or more (e.g., of solid or semi-solid composition), or another amount as known in the art.

The disclosed compositions can be administered in accordance with the methods at any frequency as a single bolus or multiple dose e.g., one, two, three, four, five, or more times hourly, daily, or weekly or for as long as appropriate. Exemplary frequencies are typically from 1-3 times, 2-times or once, daily; for example, once per day for 30 days or indefinitely. Timing of administration can be dictated by the desired characteristic to be affected, such as treating or preventing an infection caused by a primary bacterium or for reducing or preventing overpopulation of a primary bacterium (e.g., by reducing the number and/or concentration of the primary bacterium in the treatment space). The skilled artisan will appreciate the factors that may influence the dosage, frequency, and timing required to provide an amount sufficient or effective for providing the desired effect or benefit. Dosage and administration can be adjusted to provide sufficient levels of the one or more bacteriophage (collectively or individually) or to maintain the desired effect.

In at least one embodiment, the composition can be administered or received as part of a treatment protocol. The treatment protocol can include a first treatment period (or phase). The first treatment phase can include a first dosage of the composition, administered or received in accordance with a first dosage schedule. The first dosage schedule can be, for example, a daily dosage schedule or any other suitable dosage schedule (e.g., twice daily, every other day, once weekly, twice weekly, etc.). The first dosage can include any suitable dose (amount) disclosed herein. In at least one embodiment, the first dose (amount) of the first dosage in the first treatment phase can be or include a (relatively high) initial treatment dose (e.g., greater than or equal to $1\times10^6$, $1\times10^7$, $1\times10^8$, $1\times10^9$, or $1\times10^{10}$ PFU/mL or PFU/mg of the one or more bacteriophage in addition to and/or separate from $1\times10^6$, $1\times10^7$, $1\times10^8$, $1\times10^9$, or $1\times10^{10}$ CFU/mL or CFU/mg of the one or more bystander bacteria. In some embodiments, the first dosage phase (or schedule thereof) can be or last for any suitable amount of time (e.g., greater than or equal to 1 week, 2 weeks, 3 weeks, 4 weeks, 1 month, 2 months, 3 months, 6 months, 9 months, 1 year, etc.).

In some embodiments, the treatment protocol can include a second treatment period (or phase). The second treatment period can include a second dosage of the composition, administered or received in accordance with a second dosage schedule. The second dosage schedule can be, for example, a weekly dosage schedule or any other suitable dosage schedule (e.g., daily, every other day, twice weekly, etc.). The second dosage can include any suitable dose disclosed herein. In at least one embodiment, the second treatment phase can include a (lower) maintenance treatment dose (e.g., greater than or equal to $1\times10^4$, $1\times10^5$, $1\times10^6$, $1\times10^7$, or $1\times10^8$ PFU/mL or PFU/mg of one or more bacteriophage and/or greater than or equal to $1\times10^4$, $1\times10^5$, $1\times10^6$, $1\times10^7$, or $1\times10^8$ CFU/mL or CFU/mg of one or more bystander bacterium). Illustratively, the second dosage can include a lower concentration of bacteriophage and/or bystander bacterium than the first dosage. Alternatively, or in addition, the second treatment phase can include a less frequent dosage schedule than the first treatment phase. In some embodiments, the second dosage phase (or schedule thereof) can be or last for any suitable amount of time (e.g., greater than or equal to 3 months, 6 months, 9 months, 1 year, 2 years, 3 years, etc., or indefinitely).

It should be appreciated that the first and second dosages and/or first and second treatment periods can be, respectively, a dosage and/or treatment period of one or more bystander bacterium or one or more bacteriophage (or vice versa).

In some embodiments, a composition containing one or more bacteriophages is co-administered with one or more bystander bacteriophages, a probiotic, and/or prebiotic.

Abbreviated List of Defined Terms

To assist in understanding the scope and content of the foregoing and forthcoming written description and appended claims, a select few terms are defined directly below. Unless defined otherwise, all technical and scientific terms used herein have the same meaning as commonly understood by one of ordinary skill in the art to which the present disclosure pertains.

The terms "bacteriophage" or "phage," as used herein, include any prokaryotic virus that infect bacteria. "Bacteriophage" and "phage" are used interchangeably and can include naturally-occurring and recombinant bacteriophages, unless otherwise indicated. A "naturally-occurring" bacteriophage is a phage isolated from a natural or human-made environment that has not been modified by genetic engineering. A "recombinant bacteriophage" is a phage that comprises a genome that has been genetically modified by insertion of a heterologous nucleic acid sequence into the genome or by removal of a nucleic acid sequence from the genome. The genome of a naturally-occurring phage may be modified by recombinant DNA technology to introduce a heterologous nucleic acid sequence into the genome at a defined site. Additionally, or alternatively, the genome of a naturally-occurring phage may be modified by recombinant DNA technology to remove nucleic acid sequences that, for example, encode bacterial virulence factors (e.g., toxins). A further description of bacteriophages can be found in U.S. Pat. No. 9,617,522, the entirety of which is incorporated by reference herein.

As used herein, the term "bystander bacterium" is intended to encompass those bacteria that are the direct target of an administered bacteriophage and that genetically encode a bacteriotoxin expressed upon infection by the administered bacteriophage. The bystander bacterium generally does not directly contribute to and/or cause pathology and is generally not the target of therapeutic intervention. Bystander bacteria can be added to the treatment space prior to, after, or co-administered with the bacteriophage. Alternatively, bystander bacteria can be residents of a host microbiome.

The term "co-administration" and similar terms refer to concurrent, sequential, and/or combined administration of two or more components. For instance, two components can be co-administered by administering each component in a separate dosage concurrently, simultaneously, or sequentially (e.g., distinct administrations separated by a period of time). The period of time can be very short (e.g., substantially immediately following a first administration) or it may be longer (e.g., 10-60 seconds later, 1-60 minutes later, 1-24 hours later, 1-7 days later, or any value or range of values therebetween). Concurrent or simultaneous administration can include overlapping administration timeframes for the two or more components or administration of a combination product comprising a mixture of the two or more components.

As used herein, the term "cocktail," "bacteriophage cocktail, "phage cocktail," or similar is intended to be understood as a composition that includes two or more bacteriophages. The composition may have a proportional or disproportional number or concentration of phages, and the phages comprising the cocktail may have overlapping or non-overlapping tropisms. The cocktail can be in a dry form or suspended in a pharmaceutically-acceptable carrier.

A "live culture," as that term is used herein, is intended to include a population of organisms that are (i) metabolically active, (ii) in a metabolically quiescent state but that are capable of returning to metabolic activity, or (iii) actively replicating or capable of replicating. In contrast, a dead culture includes metabolically inactive cells that have inactivated such as by heat inactivation, chemical inactivation, or other The term "microbiome," which may be used synonymously with the term "microbiota" generally refers to the population, collection, and/or totality of microbes in a defined environment, habitat, or ecological community, and typically includes a plurality of genera, species, or strains of commensal, symbiotic, beneficial, and/or opportunistic pathogenic microorganisms (e.g., bacteria, archaea, fungae, protists, and/or viruses), and typically including their genetic elements (e.g., genomic nucleic acid).

As used herein, the term "primary bacterium" is intended to encompass those bacteria that are the target of therapeutic intervention and that are the causative agent of—or contribute to—disease or that are otherwise targeted for a reduction in the total number and/or concentration of bacteria within a host and/or environment. For example, primary bacteria include—but are not limited to—pathogenic bacteria and opportunistic pathogens susceptible to the bacteriotoxins produced by infected bystander bacteria.

The term "prebiotic" generally refers to a component (e.g., an energy source or food, food ingredient, dietary supplement, etc.) that when consumed by a non-human animal stimulates the growth, diversity, or activity of at least a subset of microbes within the animal's microbiome. In some instances, the prebiotic can be selected to include a preferred food source for one or more bacteria within the subject's intestinal microbiome and/or within a co-administered probiotic to encourage the growth or activity of that population of microbes.

The term "probiotic" generally refers to one or more live microbes associated with neutral or beneficial effects in the mammalian gastrointestinal tract. An exemplary probiotic can include one or more of *Lactobacillus* sp., *Bifidobacterium* sp., *Saccharomyces* sp., and/or a component (e.g., a food, food ingredient, dietary supplement, etc.) that includes the same. Typically, when consumed, a probiotic can assist in maintaining or restoring beneficial levels, diversity, or activity, of the microbiome.

As used herein, the term "tropism" is understood as the host range, number, and/or type of bacteria that a given bacteriophage may successfully infect. For the purposes of this disclosure, a "successful" infection comprises the ability of the bacteriophage to interact with the bacterial host and cause expression of the host's genomically-encoded bacteriotoxin regardless of the bacteriophage lifecycle (i.e., lytic or lysogenic). Typically, this interaction includes adsorption of the bacteriophage to the bacterial cell surface and subsequent injection of phage nucleic acid into the host cell.

Some bacteriophages are understood to have broad microbial tropism, being capable of successfully infecting bacteria from different phylogenetic orders and/or greater than 10, preferably greater than 8, or more preferably greater than 6 different genera and/or species of bacteria within the same phylogenetic order, while other bacteriophages have a narrower tropism, being capable of successfully infecting, preferably, bacteria from the same phylogenetic order, more preferably only select genera and/or species of bacteria. In some instances, a bacteriophage may have a narrow tropism for bacteria derived from a single genera or bacterial species or strain. A bacteriophage having a "narrow tropism" is understood to be capable of successfully infecting less than or equal to 6, preferably less than or equal to 5, or more preferably less than or equal to 4, still more preferably less than or equal to 3, still more preferably less than or equal to 2, most preferably a single bacterial genera and/or species or strain.

CONCLUSION

Any headings used herein are for organizational purposes only and are not meant to be used to limit the scope of the description or the claims.

It will be appreciated that systems, devices, products, kits, methods, and/or processes, according to certain embodiments of the present disclosure may include, incorporate, or otherwise comprise properties, features (e.g., components, members, elements, parts, and/or portions) described in other embodiments disclosed and/or described herein. Accordingly, the various features of certain embodiments can be compatible with, combined with, included in, and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include said features, members, elements, parts, and/or portions without necessarily departing from the scope of the present disclosure.

Likewise, any steps recited in any method or process described herein and/or recited in the claims can be executed in any suitable order and are not necessarily limited to the order described and/or recited, unless otherwise stated (explicitly or implicitly). Such steps can, however, also be performed in a specific order or any suitable order in certain embodiments of the present disclosure.

The present disclosure may be embodied in other specific forms without departing from its spirit or essential characteristics. The described embodiments are to be considered in all respects only as illustrative and not restrictive. The scope of the invention is, therefore, indicated by the appended claims rather than by the foregoing description. While certain embodiments and details have been included herein and in the attached disclosure for purposes of illustrating embodiments of the present disclosure, it will be apparent to those skilled in the art that various changes in the compositions and kits disclosed herein may be made without departing from the scope of the disclosure or of the invention, which is defined in the appended claims. All changes which come within the meaning and range of equivalency of the claims are to be embraced within their scope.

What is claimed is:

1. A method comprising:

administering live, *Brevibacillus laterosporus* bacteria to a honeybee exhibiting American foulbrood; and administering at least one bacteriophage tropic for the *Brevibacillus laterosporus* bacteria to the honeybee, the *Brevibacillus laterosporus* bacteria having a genomically-encoded bacteriotoxin that is expressed upon infection by the at least one bacteriophage, the bacteriotoxin having specificity for at least a primary bacterium causing the American foulbrood.

2. The method of claim 1, wherein administering the at least one bacteriophage comprises administering a plurality of different bacteriophages.

3. The method of claim 2, wherein each of the plurality of different bacteriophages is tropic for the *Brevibacillus laterosporus* bacteria.

4. The method of claim 1, wherein the primary bacterium comprises *Paenibacillus larvae.*

5. The method of claim 1, wherein the step of administering the live, *Brevibacillus laterosporus* bacteria comprises administering two or more strains of live, *Brevibacillus laterosporus* bacteria.

6. A method, comprising:

administering live *Brevibacillus laterosporus* to *Apis mellifera* having an infection or infestation of *Paenibacillus larvaei*; and administering a bacteriophage tropic for the *Brevibacillus laterosporus* to the *Apis mellifera,* the *Brevibacillus laterosporus* expressing a bacteriotoxin having specificity for *Paenibacillus larvaei* upon infection by the bacteriophage.

* * * * *